(12) United States Patent
Kobuke et al.

(10) Patent No.: US 7,022,840 B2
(45) Date of Patent: *Apr. 4, 2006

(54) PORPHYRIN ARRAY EXHIBITING LARGE TWO PHOTON ABSORPTION PROPERTY AND INCLUDING, AS STRUCTURAL UNIT, BIS (IMIDAZOLYLPORPHYRIN METAL COMPLEX) LINKED WITH ACETYLENIC BOND AND THE DERIVATIVE THEREOF, AND METHOD OF PRODUCING THE SAME

(75) Inventors: Yoshiaki Kobuke, Ikoma (JP); Kazuya Ogawa, Ikoma (JP)

(73) Assignee: Nara Institute of Science and Technology, Ikoma (JP)

( * ) Notice: Subject to any disclaimer, the term of this patent is extended or adjusted under 35 U.S.C. 154(b) by 123 days.

This patent is subject to a terminal disclaimer.

(21) Appl. No.: 10/715,493

(22) Filed: Nov. 19, 2003

(65) Prior Publication Data

US 2004/0106787 A1 Jun. 3, 2004

(30) Foreign Application Priority Data

Nov. 19, 2002 (JP) ............................. 2002-335246

(51) Int. Cl.
*A61B 5/055* (2006.01)
*A61B 10/00* (2006.01)
*C07B 47/00* (2006.01)
*C07F 5/10* (2006.01)
*A61K 31/555* (2006.01)

(52) U.S. Cl. .................. 540/145; 424/9.362; 424/9.61; 534/15; 514/185; 514/410

(58) Field of Classification Search ............. 424/9.362, 424/9.61; 540/145; 534/15; 514/185, 410
See application file for complete search history.

(56) References Cited

U.S. PATENT DOCUMENTS

| 6,429,310 | B1 | 8/2002 | Kobuke et al. | |
| 6,602,998 | B1 | 8/2003 | Kobuke et al. | |
| 2003/0187251 | A1* | 10/2003 | Kobuke et al. | ............. 540/145 |
| 2004/0072988 | A1 | 4/2004 | Kobuke et al. | |
| 2004/0202876 | A1 | 10/2004 | Kobuke et al. | |

OTHER PUBLICATIONS

Screen et al., Amplified Optical Nonlinearity in a Self-Assembled Double-Strand Conjugated Porphyrin Polymer Ladder., Jul. 27, 2002, J. Am. Chem. Soc. 2002. 124 pp. 9712-9713.*
Ogawa et al., Formation of a Giant Supramolecular Porphyrin Array by Self-Coordination., 2000. Agnew. Chem. Int. vol. 39(22) pp. 4070-4073.*
Ogawa et al. Formation of a Giant upramolecular Porphyrin Array by Self Coordination. Angew. Chem. Int. Ed. 2000. 39 No. 22. pp. 4070-4073.*

Screen et al. Amplified Optical Nonlinearity in a Self-Assembled Double-Strand Conjugated Porphyrin Polymer Ladder. J. Am. Chem. soc. 2002., 124., pp. 9712-9713.*
M. Albota, et al., Science, www.sciencemag.org., vol. 281, pp. 1653-1656, "Design of Organic Molecules With Large Two-Photon Absorption Cross Sections", Sep. 11, 1998.
T. E. O. Screen, et al., J. Am. Chem. Soc., vol. 124, No. 33, pp. 9712-9713, "Amplified Optical Nonlinearity in a Self-Assembled Double-Strand Conjugated Porphyrin Polymer Ladder", 2002.
K. Ogawa, et al., Angew. Chem. Int. vol. 39, No. 22, pp. 4070-4073, "Formation of a Giant Supramolecular Porphyrin Array by Self-Coordination", 2000, (with corr. US 6,429,310).
K. Ogawa, et al., J. Am. Chem. Soc., vol. 124, No. 1, pp. 22-23, "Large Third-Order Optical Nonlinearity of Self-Assembled Porphyrin Oligomers", 2002, (with corr. U.S. Appl. No. 10/231,074).
K. Ogawa, et al., J. Am. Chem. Soc., vol. 125, No. 44, pp. 13356-13357, "Strong Two-Photon Absorption of Self-Assembled Butadiyne-Linked Bisporphyrin", 2003 (with corr. U.S. Appl. No. 10/715,493).

* cited by examiner

*Primary Examiner*—James O. Wilson
*Assistant Examiner*—Matthew L. Fedowitz
(74) *Attorney, Agent, or Firm*—Oblon, Spivak, McClelland, Maier & Neustadt, P.C.

(57) ABSTRACT

A porphyrin array exhibiting a large two-photon absorption property, and being linked with an acetylenic bond(s), represented by the following formulas:

-continued

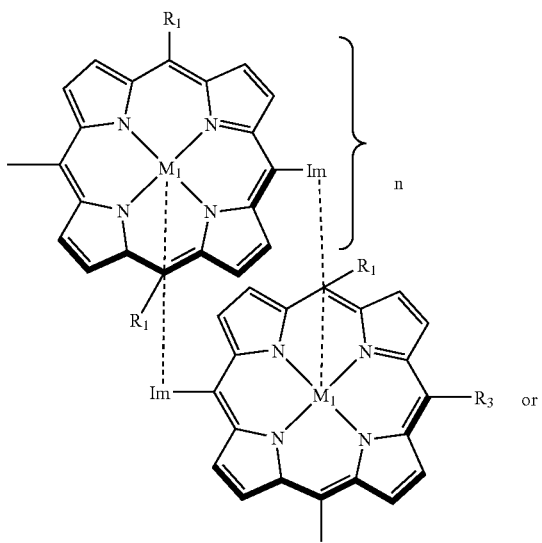

(1-2)

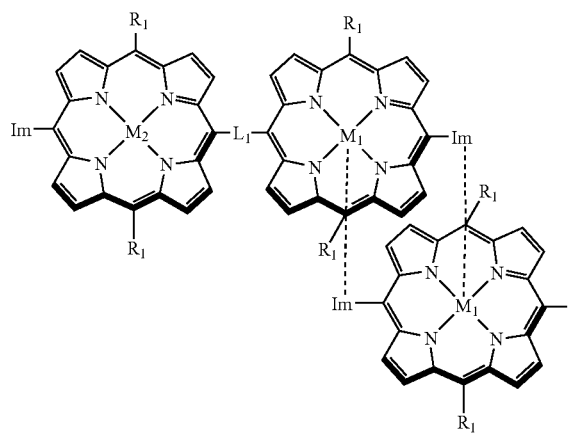

-continued

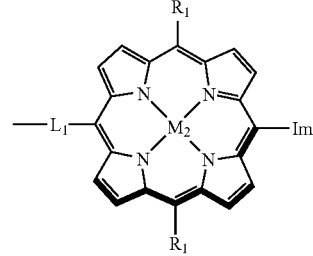

wherein $R_1$ represents an alkyl or aryl group, $M_1$ represents a metal ion capable of serving as a core metal and forming a coordinate bond with Im, $M_2$ represents two protons or a metal ion incapable of forming a coordinate bond with Im, $R_2$ and $R_3$ represent a group selected from a porphyrin residue or porphyrin metal complex residue, a cyclic diimide residue, a dialkylviologen residue, a benzoquinone residue, an N-methylpyrrolidine-fullerene derivative residue and a ferrocene residue, Im is represented by $Im_1$ or $Im_2$:

($R_8$ represents methyl or H), $L_1$ represents $-(-C{\equiv}C-)_m-$ (m=1 to 3); n represents an integer of 1 or more; $R_9$ represents one of $R_1$, $R_2$, $R_3$ and Im.

9 Claims, 6 Drawing Sheets

PORPHYRIN ARRAY EXHIBITING LARGE TWO PHOTON ABSORPTION PROPERTY AND INCLUDING, AS STRUCTURAL UNIT, BIS (IMIDAZOLYLPORPHYRIN METAL COMPLEX) LINKED WITH ACETYLENIC BOND AND THE DERIVATIVE THEREOF, AND METHOD OF PRODUCING THE SAME

CROSS-REFERENCE TO RELATED APPLICATIONS

This application is based upon and claims the benefit of priority from the prior Japanese Patent Application No. 2002-335246, filed Nov. 19, 2002, the entire contents of which are incorporated herein by reference.

BACKGROUND OF THE INVENTION

1. Field of the Invention

The present invention relates to porphyrin metal complexes which can serve as two-photon absorption materials, and derivatives thereof. More specifically, the present invention relates to porphyrin arrays which exhibit large two-photon absorption, and having, as a structural unit, bis (imidazolylporphyrin metal complex) linked with an acetylic bond, and derivatives thereof. The present invention also relates to porphyrin arrays having, as a structural unit, the bis(imidazolylporphyrin metal complex) that is further fixed with covalent bonds.

2. Description of the Related Art

It is expected that a two-photon absorption material will be applied to various applications such as three-dimensional optical memory, photodynamic therapy, optical limiting materials, and a two-photon microscopy. Among these applications, three-dimensional optical memory which enables ultrafast reading and writing with a very high density, and photodynamic therapy in which only cancer cells are selectively attacked by laser for medical treatment, are particularly important in view of a great contribution to the society.

In designing an organic compound exhibiting a relatively large two-photon absorption cross section, it is presumably very important that π-electron conjugated system is expanded thereby the overlap of the orbitals is increased, and polarization of the molecule is enhanced by appropriately combining an electron donor and an electron acceptor. As porphyrin is a ring-shaped tetra pyrrole in which four pyrrole nucleuses are cross-linked by four methine groups, and has a large conjugated system including 18 π-electrons, porphyrin is one of the promising candidates of the two-photon absorption materials.

The phenomenon of two-photon absorption itself has been known for years, but advanced research on two-photon absorption has finally begun since Jean-Luc Brédas et al. revealed the relationship between the molecular structure and the mechanism of two-photon absorption in 1998 (Science, 281, 1653 (1998)). However, there are few reports on the two-photon absorption of porphyrin. Quite recently, Anderson reported that a one-dimensional linear porphyrin polymer, in which porphyrins are linked with butadiyne bonds, exhibits a relatively large two-photon absorption cross section (J. Am. Chem. Soc., 124, 9712 (2002)). However, the length of the polymer cannot be adjusted, because covalent bonds are used for the linkages in the porphyrin polymer. Further, as introduction of hetero metals thereto and introduction of electron donors/electron acceptors to the terminal groups thereof is difficult, the two-photon absorption property of the porphyrin polymer cannot be further improved. Yet further, in Anderson's case, the two-photon absorption property is measured on the time scale of picoseconds, and the analysis of two-photon absorption in the order of femtoseconds, which essentially requires for an ultra fast recording, has not been carried out. As long as covalent bonds are used for the linkage of porphyrins, introduction of electron donors or electron acceptors, which enables large two-photon absorption, to a one-dimensional linear porphyrin array, was difficult. Therefore, in the conventional method of preparing porphyrin arrays, there is no prospect of achieving large two-photon absorption.

BRIEF SUMMARY OF THE INVENTION

One object of the present invention is to provide a material exhibiting large two-photon absorption, capable of simply controlling the molecular length by utilizing a coordinate bond-based self-organization reaction, which was impossible by using a covalent bond, and capable of attaching electron acceptor molecules or electron donor molecules at terminals of the molecule.

In order to achieve the objects described above, the inventors of the present invention at first linked two imidazolyl porphyrins, i.e., two porphyrins to each of which an imidazolyl group is attached, with an acetylenic bond, thereby to prepare a bis-acetylen-type dimer. Then, the inventors prepared mono-metalated complex of the bis-acetylen-type dimer, i.e., one of which is a metal complex, as a donor, and the other of which is a free base porphyrin, as an acceptor. Above mentioned two mono-metalated complexes gave a dimer formed by coordinate bonds. Prior to the discovery on which the present invention is based, the inventors had discovered the followings. That is, by coordinating a metal atom of one imidazolylporphyrin metal complex with a nitrogen atom of an imidazolyl group of another imidazolylporphyrin metal complex, a coordinated imidazolylporphyrins was prepared. Then, effecting meso-type crosslinking between two coordinated imidazolylporphyrin dimers, a meso-type poly(porphyrin) in which imidazolylporphyrin dimers were linked by coordinate bonds was prepared. It was found that the coordinate bonds of the thus prepared meso-type poly(porphyrin) can be formed and cut off by adding and removing methanol or pyridine thereto and therefrom, respectively. In order to evaluate the effect of expanding the conjugated system by the bis-acetylenic bond on the two-photon absorption property, the inventors compared an self-assembly formed with two mono-metalated-bis-acetylen-type dimeric porphyrins having free base porphyrins serving as electron acceptors at terminals thereof with another self-assembly formed with two mono-meta-lated-meso-type dimeric porphyrins. It was revealed that the self-assembly constituted of two mono-metalated-bis-acetylen-type dimers, whose conjugation system had been expanded, exhibited approximately 20 times larger two-photon absorption than the self-assembly constituted of a mono-metalated-meso-type porphyrin dimers, whose conjugation system had not been expanded. The present invention has been completed on the basis of the aforementioned discoveries.

The present invention provides: a porphyrin array exhibiting a large two-photon absorption property and being linked with an acetylenic bond represented by the following formula (1-1) or (1-2); and a method of producing the porphyrin array set forth below.

(1) A porphyrin array exhibiting a large two-photon absorption property, and being linked with an acetylenic bond(s), represented by formula (1-1) or (1-2):

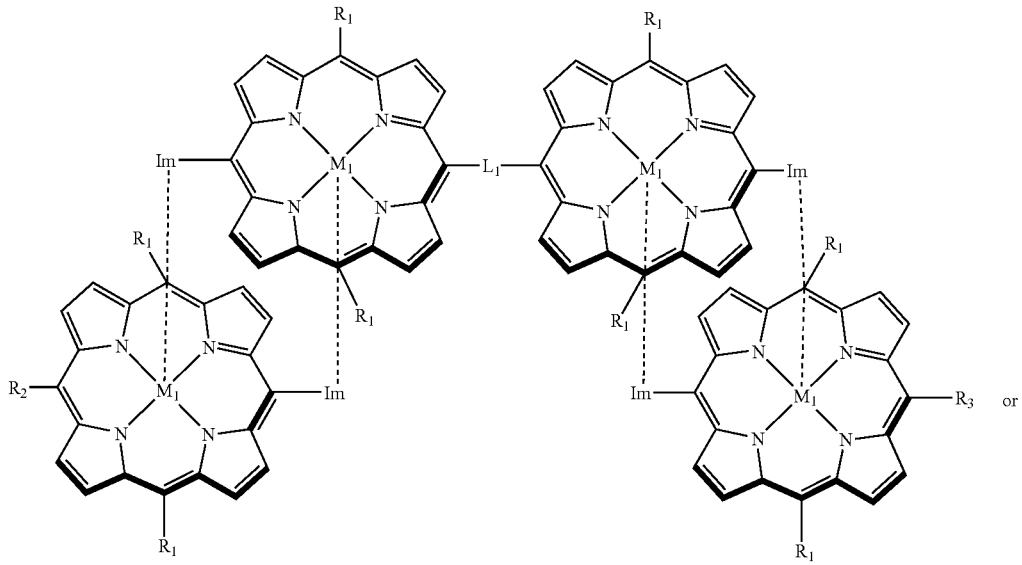

(1-1)

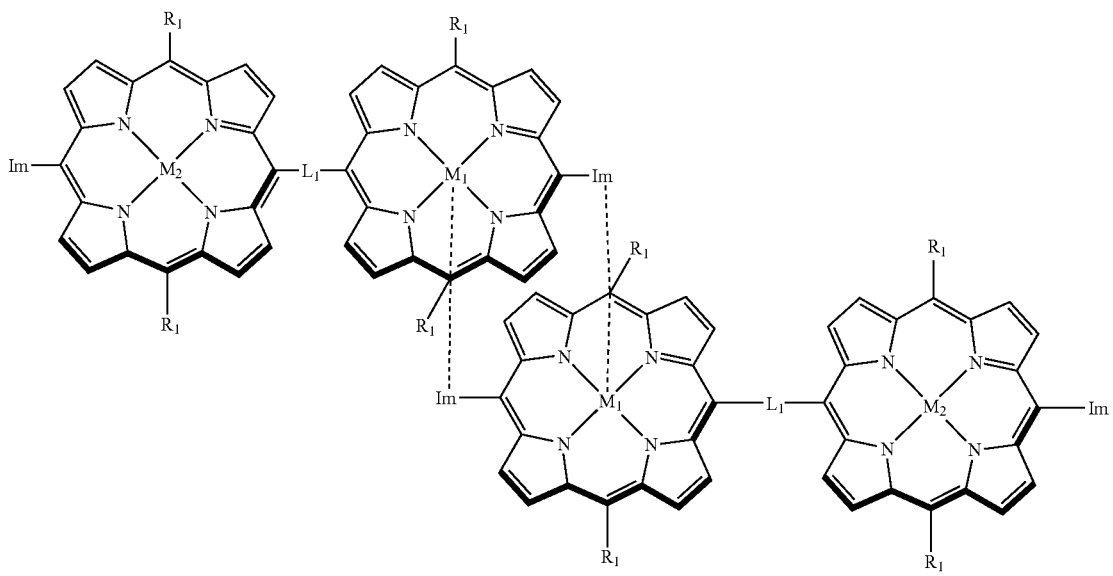

(1-2)

In the formulas (1-1) and (1-2), $R_1$ represents a substituted or unsubstituted alkyl group or substituted or unsubstituted aryl group;

$M_1$ represents a metal ion capable of serving as a core metal of the porphyrin ring and forming a coordinate bond with the imidazolyl group represented by Im; $M_2$ represents either two protons or a metal ion incapable of forming a coordinate bond with the imidazolyl group represented by Im;

$R_2$ and $R_3$ may be the same or different, and each independently represent a group selected from the group consisting of (a) to (f):

(a) a porphyrin residue without a core metal or porphyrin complex residue having a core metal represented by $M_1$ or $M_2$, (b) a cyclic diimide residue, (c) a dialkylviologen residue, (d) a benzoquinone residue, (e) an N-methylpyrrolidine-fullerene derivative residue and (f) a ferrocene residue;

Im is an imidazolyl group represented by $Im_1$ or $Im_2$:

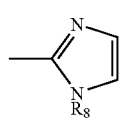

($Im_1$)

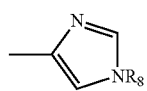

($Im_2$)

(wherein $R_8$ represents a methyl group or hydrogen atom); $L_1$ represents a linking group represented by $(—C\equiv C—)_m$ (wherein m represents an integer of 1 to 3); and n represents an integer of 1 or more.

(2) The porphyrin array described in the aforementioned (1), wherein the residues (a), (b), (c), (d), (e) and (f) are represented by:

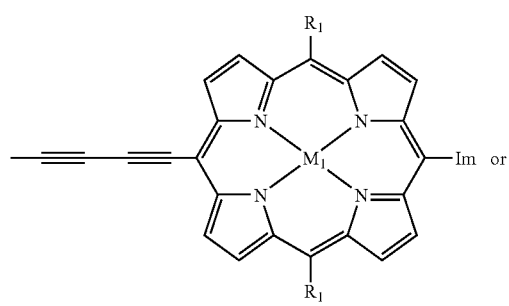

wherein $R_1$, $M_1$, $M_2$ and Im have the same meaning as defined in the aforementioned (1), $R_4$ and $R_6$ each independently represent an alkylene group or arylene group, and $R_5$ and $R_7$ each independently represent an alkyl group, alkoxyalkyl group, alkoxycarbonyl group or aryl group.

(3) The porphyrin array described in the aforementioned (1) or (2), wherein, $M_1$ is an ion of metal selected from the group consisting of zinc, iron, cobalt, ruthenium and gallium.

(4) The porphyrin array described in any one of the aforementioned (1) to (3), wherein the substituted alkyl group represented by $R_1$ is selected from the group consisting of an alkoxycarbonylalkyl group, alkoxyalkyl group, alkenoxyalkyl group and an alkenoxycarbonylalkyl group, and the substituted aryl group represented by $R_1$ is selected from the group consisting of an alkylaryl group, alkoxyaryl group, alkoxycarbonylaryl group, alkenoxyaryl group and alkenoxycarbonylaryl group.

(5) The porphyrin array described in any one of the aforementioned (1) to (4), wherein the number of carbon atoms of the substituted or unsubstituted alkyl group represented by $R_1$ is 1 to 24, and the number of carbon atoms of the substituted or unsubstituted aryl group represented by $R_1$ is 6 to 24.

(6) The porphyrin array described in any one of the aforementioned (1) to (5), wherein the number of carbon atoms of the alkyl group or the alkylene group represented by $R_4$ to $R_7$ is 1 to 20, the number of carbon atoms of the alkoxyalkyl group or the alkoxycarbonyl group represented by $R_5$ and $R_7$ is 2 to 21, and the number of carbon atoms of the aryl group or the arylene group represented by $R_4$ to $R_7$ is 6 to 20.

The present invention also provides a method of preparing the porphyrin array as follows:

(7) A method of preparing the porphyrin array represented by the formula (1-1) or (1-2) described in (1) mentioned above, comprising:

reacting, in the presence of a polar solvent, an imidazolylporphyrin metal complex represented by the following formula (2),

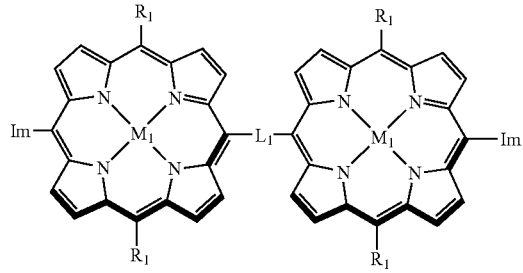

(2)

wherein $R_1$, $M_1$, $L_1$ and Im have the same meaning as defined in (1) mentioned above with an imidazolylporphyrin metal complex represented by the following formula (3),

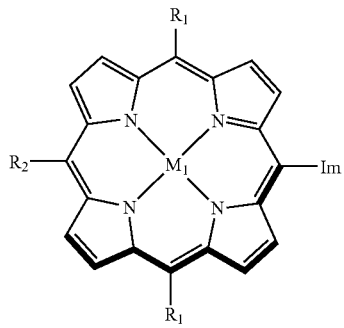

(3)

wherein $R_1$, $R_2$, $M_1$ and Im have the same meaning as defined in the aforementioned (1).

The present invention also provides a porphyrin array being linked with an acetylenic bond(s) and also being fixed with a covalent bond(s) as follows:

(8) A porphyrin array exhibiting a large two-photon absorption property, and being fixed with a covalent bond(s), represented by formula (4):

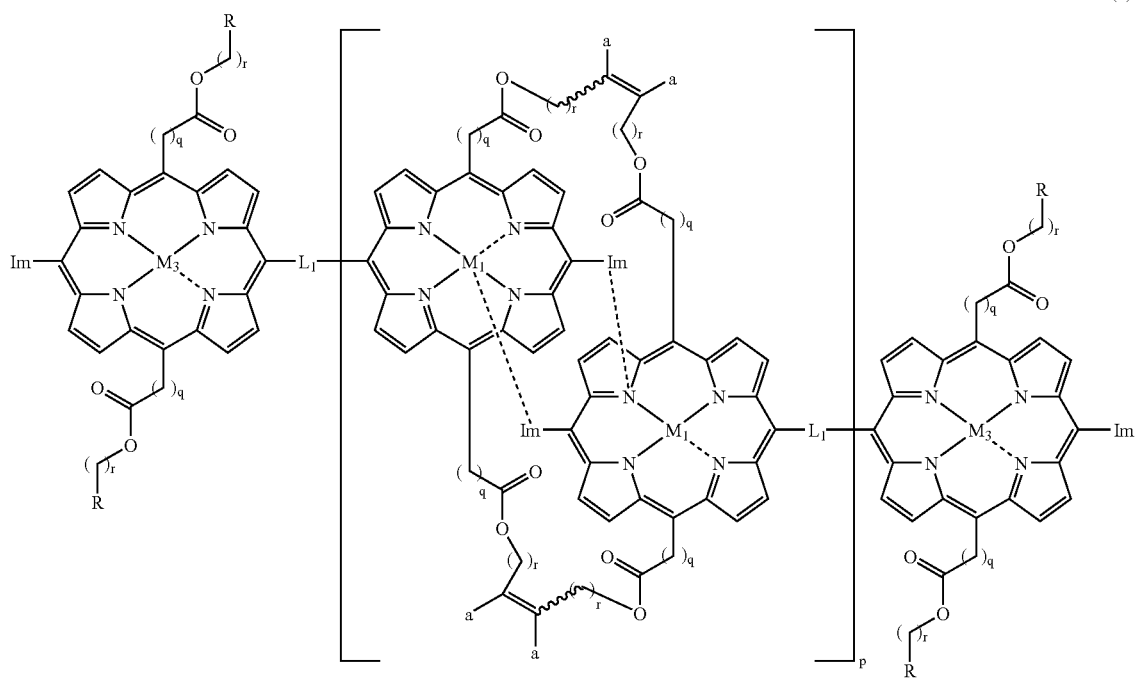

(4)

wherein R represents an alkyl group or a group as shown below:

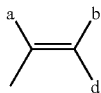

(wherein a, b and c independently represent H, an alkyl group or aryl group); $M_1$, $L_1$ and Im have the same meaning as defined in (1) mentioned above; $M_3$ represents either two protons or a metal ion selected from the group consisting of those represented by $M_1$ and $M_2$; p represents an integer of 1 or more; q represents an integer of 0 to 6; and r represents an integer of 0 to 4.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

DETAILED DESCRIPTION OF THE INVENTION

Figure 1:
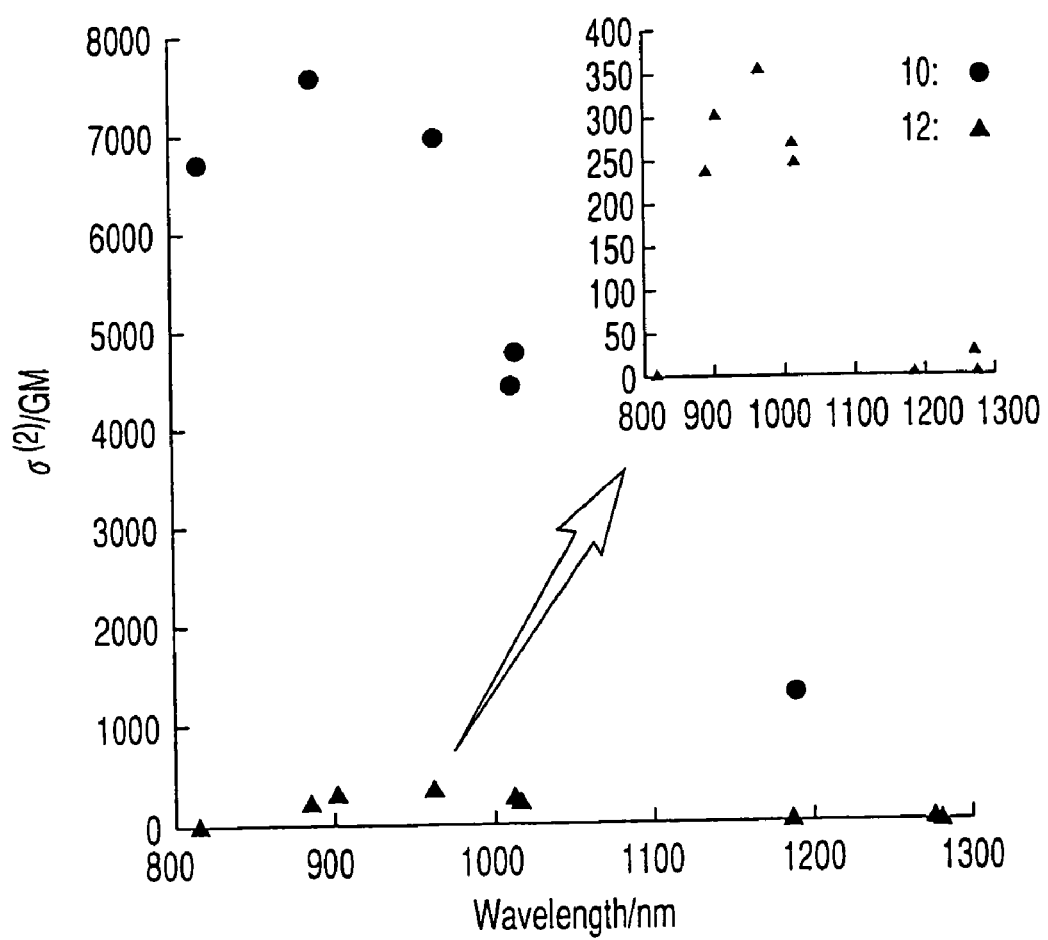
FIG. 1 is two-photon absorption spectra of a porphyrin array 10 of the present invention and a reference array 12.

First, a porphyrin array including, as a structural unit, bis(imidazolylporphyrin metal complex) or derivative thereof having an acetylenic bond for connecting the two imidazolylporphyrin metal complexes or derivatives thereof, exhibiting large two-photon absorption and represented by the formula (1-1) or (1-2) will be described in detail.

Following description on the formula (1-1) will basically be applied to the formulas (1-2), (2), (3) and (4) as well, unless otherwise mentioned.

In the above-mentioned formula (1-1), $M_1$ represents an ion of metal which is capable of being the core metal of the porphyrin ring and forming a coordinate bond with the imidazolyl group represented by Im. Specific examples of the metal ion represented by $M_1$ include Zn (II), Ga (III), Fe (II/III), Co (II/III), and Ru (II/III). However, the metal ion represented by $M_1$ is not limited to these, as long as the metal ion is capable of being the core metal of the porphyrin ring and forming a coordinate bond with the imidazolyl group expressed as Im. Among the metal ions, Zn(II) is preferable in consideration of ease in the synthesis.

In the formula (1-2), $M_2$ represents either two protons or an ion of metal which is incapable of forming a coordinate bond with the imidazolyl group. Examples of the metal ion represented by $M_2$ include gold ion, nickel ion, and copper ion. However, the metal ion represented by $M_2$ is not limited to these. $M_2$ preferably represents two protons, in consideration of ease in the synthesis.

In the formula (1-1), $R_1$ represents a substituted or unsubstituted alkyl group, or substituted or unsubstituted aryl group.

The substituted or unsubstituted alkyl group represented by $R_1$ includes normal, branched and cyclic alkyl groups.

The number of carbon atoms of the unsubstituted alkyl group or the alkyl moiety of the substituted alkyl group is not particularly limited as long as a porphyrin array represented by formula (1-1) can be formed. However, the number of carbon atoms of the unsubstituted alkyl group or the alkyl moiety of the substituted alkyl group is preferably 1 to 20, and more preferably 2 to 20, in terms of ease in production, solubility and the like.

In the case in which $R_1$ is a substituted alkyl group, examples of the substituent include an alkoxycarbonyl group, an alkoxy group, an alkenoxy group, an alkenoxycarbonyl group and the like. However, the substituent is not limited to these examples.

When $R_1$ is an alkoxycarbonylalkyl group, the number of carbon atoms of the alkoxycarbonyl moiety is not particularly limited as long as the porphyrin array can be formed. The number of carbon atoms of the alkoxycarbonyl moiety is generally in a range of 2 to 23. One example of the alkoxycarbonylalkyl group represented by $R_1$ is methoxycarbonylethyl.

When $R_1$ is an alkoxyalkyl group, the number of carbon atoms of the alkoxy moiety is not particularly limited as long as the porphyrin array can be formed. The number of carbon atoms of the alkoxy moiety is generally in a range of 1 to 22. One example of the alkoxyalkyl group represented by $R_1$ is ethoxypropyl.

When $R_1$ is an alkenoxyalkyl group, the number of carbon atoms of the alkenoxy moiety is not particularly limited as long as the porphyrin array can be formed. The number of carbon atoms of the alkenoxy moiety is generally in a range of 2 to 22. One example of the alkenoxyalkyl group represented by $R_1$ is 2-propenoxypropyl.

When $R_1$ is an alkenoxycarbonylalkyl group, the number of carbon atoms of the alkenoxycarbonyl moiety is not particularly restricted as long as the porphyrin array can be formed. The number of carbon atoms of the alkenoxycarbonyl moiety is generally in a range of 3 to 24. One example of the alkenoxycarbonylalkyl group represented by $R_1$ is 2-propenoxycarbonylethyl.

When $R_1$ is a carboxyalkyl group, one example of the carboxyalkyl group is carboxyethyl.

The substituted or unsubstituted aryl group represented by $R_1$ may be either monocyclic or in a form of fused rings.

The number of carbon atoms of the unsubstituted aryl group or the aryl moiety of the substituted aryl group is not particularly restricted as long as the porphyrin array can be formed. However, the number of carbon atoms of the unsubstituted aryl group or the aryl moiety of the substituted aryl group is preferably 6 to 20, and more preferably 6 to 10, in terms of ease in production, solubility and the like. Examples of the unsubstituted aryl group include phenyl, naphtyl, but the unsubstituted aryl group represented by $R_1$ is not limited to these.

When $R_1$ is a substituted aryl group, examples of the substituent include an alkyl group, alkoxy group, alkoxycarbonyl group, alkenoxy group and alkenoxycarbonyl group. However, the substituent is not limited to these.

The number of carbon atoms of the alkyl group, alkoxy group, alkoxycarbonyl group, alkenoxy group, and alkenoxycarbonyl group as the substituent of the substituted aryl group is the same as those defined in the above-mentioned those for $R_1$. Examples of the alkylaryl group, alkoxyaryl group, alkoxycarbonylaryl group, alkenoxyaryl group and alkenoxycarbonylaryl group represented by $R_1$ is, 4-methylphenyl, 4-methoxyphenyl, 4-(ethoxycarbonyl)-phenyl, 4-(2-propenoxy)-phenyl and 4-(2-propenoxycarbonyl)-phenyl, respectively. However the substituted aryl group is not limited to these.

In the formula (1-1), there exists a plurality of substituent groups $R_1$. These $R_1$ groups may be the same or different. However, these groups are preferably the same, in terms of ease in production. The same can be applied to each of the formulas (1-1), (1-2), (2), (3) and (4), when there exist a plurality of substituent groups represented by the same symbol.

$R_1$ is preferably an alkyl group, alkyl-substituted aryl group or alkyloxy-substituted aryl group, in terms, e.g., of solubility of the resulting porphyrin array.

When $R_1$ is a group having an olefin moiety, such as an alkenoxycarbonylalkyl group, alkenoxyalkyl group, alkenoxyaryl group and alkenoxycarbonylaryl group, the group can be utilized in a cyclization metathesis reaction for producing a porphyrin array including, as a structural unit, bis(imidazolylporphyrin metal complex) fixed by covalent bonds and represented by the formula (4) of the present invention, which will be described later.

In the formula (1-1), $R_2$ and $R_3$ may be the same or different. Each of $R_2$ and $R_3$ represent a residue selected from the group consisting of: (a) a porphyrin residue without a core metal or porphyrin complex residue having a core metal represented by $M_1$ or $M_2$ mentioned above, (b) a cyclic diimide residue, (c) a dialkylviologen residue, (d) a benzoquinone residue, (e) an N-methylpyrrolidine-fullerene derivative residue and (f) a ferrocene residue.

Specific examples of the residues (a) to (f) are as follows. However, the residues (a) to (f) are not limited to these specific examples.

(a)

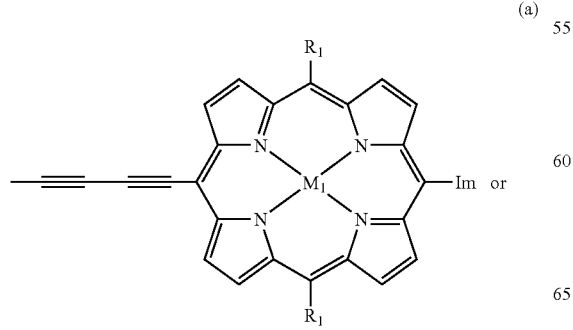

-continued

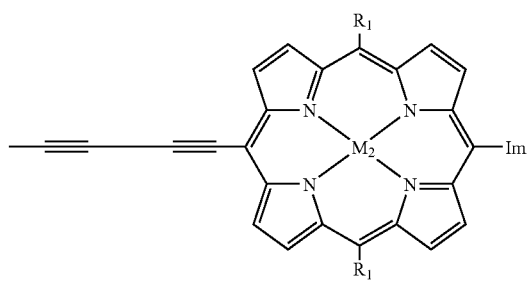

(b)

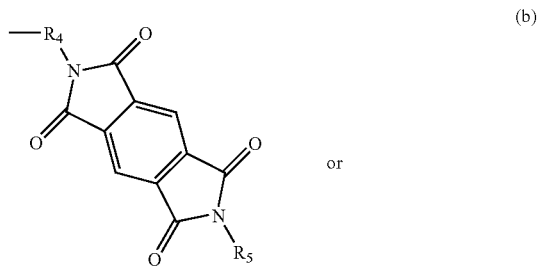

or

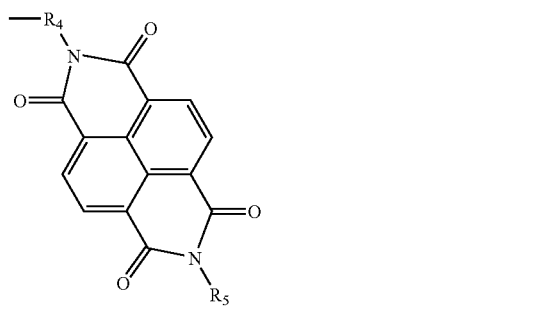

(c)

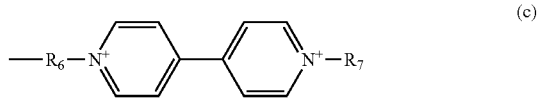

(d)

(e)

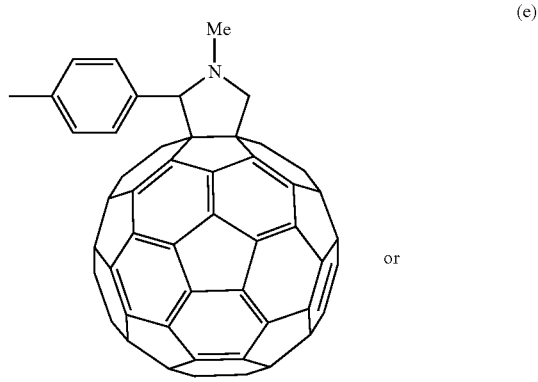

or

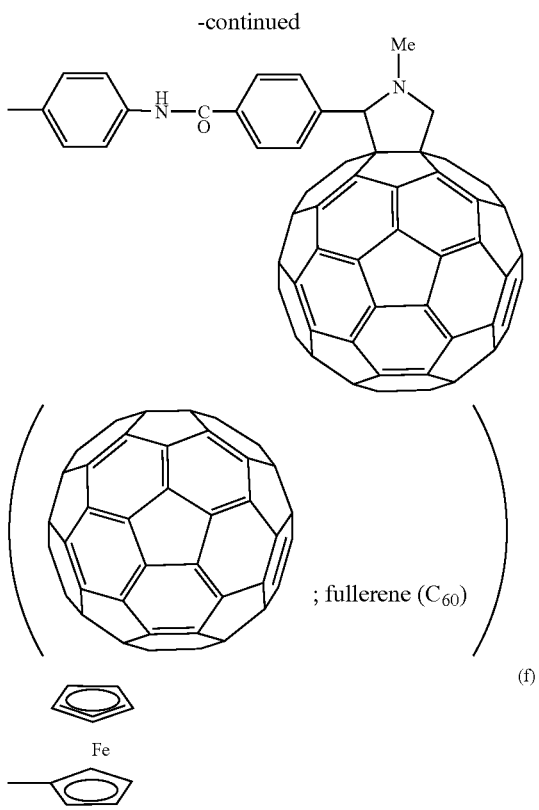

; fullerene ($C_{60}$)

(f)

In the formulas, $R_1$, $M_1$, $M_2$ and Im have the same meaning as in formulas (1-1) and (1-2). $R_4$ and $R_6$ independently represent an alkylene group or arylene group. $R_5$ and $R_7$ independently represent an alkyl group, alkoxyalkyl group, alkoxycarbonyl group or aryl group. There is no specific preference of $R_2$ and $R_3$ among the residues (a) to (f), but the residue (d), benzoquinone, may be preferably used for ease in preparation.

The number of carbon atoms of the alkylene group and arylene group represented by $R_4$ and $R_6$ is not particularly limited, as long as these groups can constitute the terminal groups of the porphyrin array. The number of carbon atoms of the alkylene group and arylene group represented by $R_4$ and $R_6$ is preferably 1 to 20 (6 to 20 in the case of arylene group), and more preferably 2 to 20 (7 to 20 in the case of arylene group).

The number of carbon atoms of the alkyl group and aryl group represented by $R_5$ and $R_7$ is not particularly limited, as long as these groups can constitute the terminal groups of the porphyrin array. The number of carbon atoms of the alkyl group and aryl group represented by $R_5$ and $R_7$ is preferably 1 to 20 (6 to 20 in the case of aryl group), and more preferably 3 to 20 (7 to 20 in the case of aryl group).

The number of carbon atoms of the alkoxyalkyl group and alkoxycarbonyl group represented by $R_5$ and $R_7$ is not particularly limited, as long as these groups can constitute the terminal groups of the porphyrin array. The number of carbon atoms of the alkoxyalkyl group and alkoxycarbonyl group represented by $R_5$ and $R_7$ preferably 2 to 20, and more preferably 3 to 20.

The compounds which provide the residues (a) to (f) represented by $R_2$ and $R_3$ are commercially available or can be synthesized from other products which are commercially available by referring to documents.

In the formula (1-1), n represents an integer of 1 or more. The upper limit of n is not particularly restricted as long as the porphyrin array can be formed. It is assumed that synthesis of a porphyrin array is possible until n reaches, for example, approximately 1000.

In the formula (1-1), $L_1$ represents an acetylenic linking group represented by $(-C\equiv C-)_m$, wherein m represents an integer of 1 to 3. However, the polyacetylene group in which m exceeds 3 or any other group may also be acceptable, as long as the porphyrin array represented by the formula (1-1) of the present invention exhibits large two-photon absorption.

As shown in the formulas (1-1) and (1-2) of the present invention, in the imidazolylporphyrin dimer as the structural unit, the imidazole ring of the imidazolyl group that bonds to each porphyrin of the dimer, is arranged so as to spread along a plane substantially perpendicular to a plane defined by the pyrrole rings and the methine groups. Further, the two porphyrin rings are linked to each other with 1 to 3 acetylenic bond(s), so that the two porphyrin rings lie on the same plane. In the formulas (1-1) and (1-2), each of the metals represented by $M_1$, $M_2$, $M_3$ and $M_4$ (except for the case in which $M_2$, $M_3$ and $M_4$ are two protons) is bonded, by coordinate bond, to the nitrogen atom of the pyrrole nucleus surrounding the metal. Yet further, the core metal $M_1$ is bonded to the nitrogen atom of the imidazoly group by a coordinate bond.

Next, a porphyrin array including, as a structural unit, bis(imidazolylporphyrin metal complex) and fixed by covalent bonds and represented by the formula (4) of the present invention (which porphyrin array will also be referred to as "the covalent bond-fixed porphyrin array of the present invention", hereinafter) will be described in detail.

The covalent bond-fixed porphyrin array of the present invention is a porphyrin array obtained by a cyclization metathesis reaction of the porphyrin array represented by the formula (1-1) of the present invention to fix the porphyrins by covalent bonds, wherein the terminal groups represented by $R_2$ and $R_3$ are the residue (a):

(a)

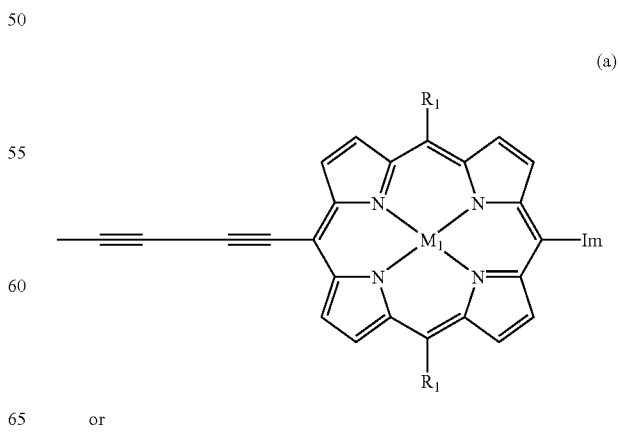

or

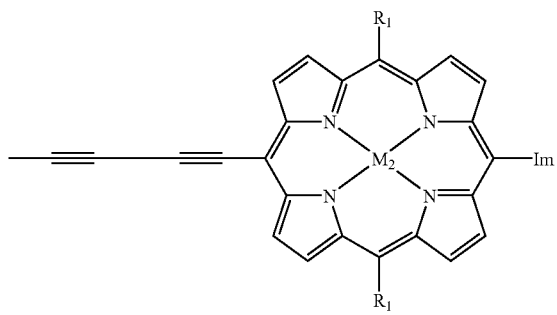

each having a core metal represented by $M_1$ or $M_2$ (wherein $R_1$, $M_1$, $M_2$ and Im have the same meaning as defined in the formula (1-1)); and at the same time, the group represented by $R_1$ is a group having an olefin residue (i.e., alkenoxyalkyl group, alkenoxycarbonylalkyl group, alkenoxyaryl group or alkenoxycarbonylaryl group).

The covalent bond-fixed porphyrin array of the present invention exhibits large two-photon absorption, in a manner similar to the porphyrin arrays of the formulas (1-1) and (1-2). In the case of the porphyrin arrays represented by the formulas (1-1) and (1-2), the coordinate bonds thereof tend to be cut off when the solvent to which the porphyrin arrays are dissolved has relatively high polarity. Therefore, the range in which the porphyrin arrays of the formulas (1-1) and (1-2) is applicable may be restricted, depending on the available medium and the environment. On the contrary, in the covalent bond-fixed porphyrin array of the present invention, as fixation thereof is effected by covalent bonds, the degree of polymerization can be maintained in the stable manner without depending on the polarity of the solvent to which the porphyrin array is dissolved, and thus the range in which the porphyrin arrays is applicable is widened, which is advantageous.

In the formula (4), R represents an alkyl group or a group represented by

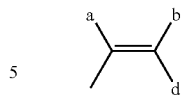

wherein a, b and c independently represent H, an alkyl group or aryl group.

$M_1$, $L_1$ and Im have the same meaning as defined in the formula (1-1). $M_3$ has the same meaning as $M_1$ or $M_2$. p represents an integer of 1 or more, q represents an integer of 0 to 6, and r represents an integer of 0 to 4.

The alkyl group represented by R, a, b and c has the same meaning as the alkyl group mentioned above for $R_1$ of the formula (1-1).

p represents an integer of 1 or more. As is the case with n of the formula (1-1), the upper limit of p is not particularly restricted unless the formation of the porphyrin array is disturbed. It is assumed that synthesis of a porphyrin array is possible until p reaches, for example, approximately 1000.

q represents an integer of 0 to 6. q is preferably 2, in consideration of ease in the synthesis of the raw material compound thereof and functions which the resulting product is supposed to have.

r represents an integer of 0 to 4. r is preferably 1, in consideration of ease in the synthesis of the raw material compound thereof and functions which the resulting product is supposed to have.

In the porphyrin array of the formula (4), the manner in which the porphyrin ring, the imidazolyl group and the core metal are bonded and configured with respect to each other is the same as that described in the formulas (1-1) and (1-2).

Hereinafter, there will be described a method of producing porphyrin arrays represented by the formula (1-1) wherein (i) both $R_2$ and $R_3$ are porphyrin zinc complex of residue (a), $M_1$ is Zn and $L_1$ is (—C≡C—)$_2$; and (ii) both $R_2$ and $R_3$ are free base porphyrin of residue (a), i.e., $M_2$ represents two protons, $M_2$ is Zn, $L_1$ is (—C≡C—)$_2$; and porphyrin arrays represented by the formula (1-2) wherein $M_1$ is Zn and $M_2$ represents two protons. Other porphyrin arrays of the present invention having other substituents may also be synthesized in a manner similar to this.

The porphyrin array of the present invention in which $M_1$ is Zn(II), and both $R_2$ and $R_3$ are free base porphyrins may be prepared by the following step 1 to step 8, but the preparation method is not limited to this.

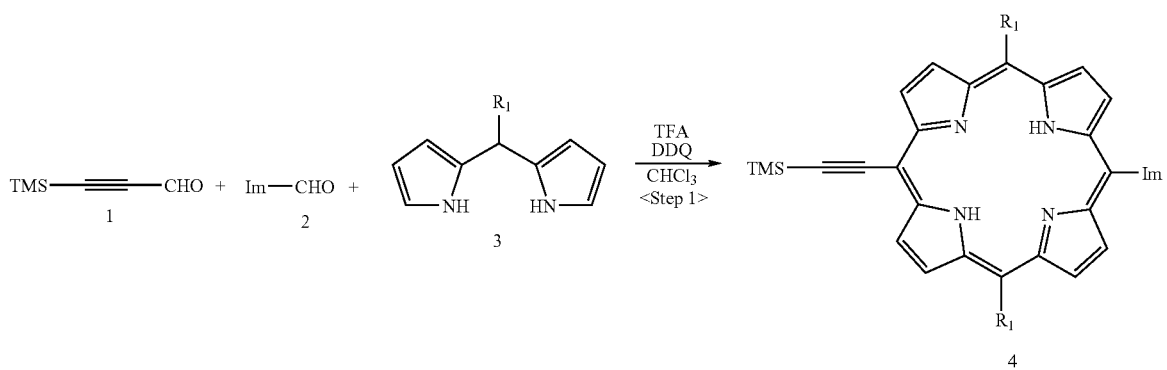

-continued
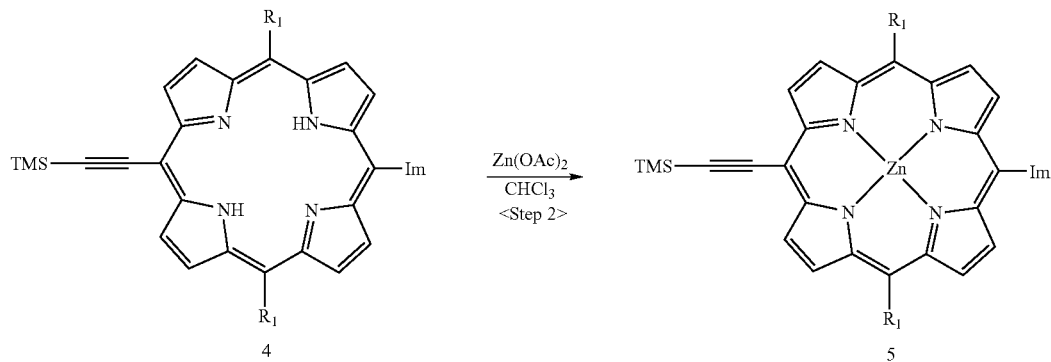
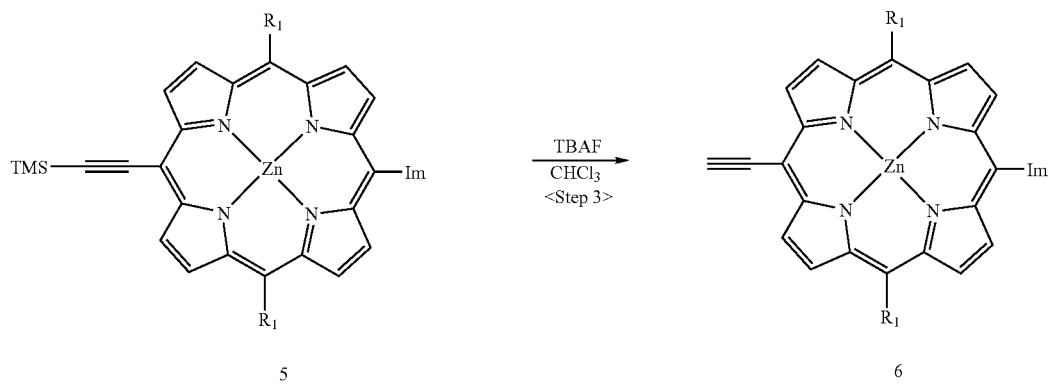
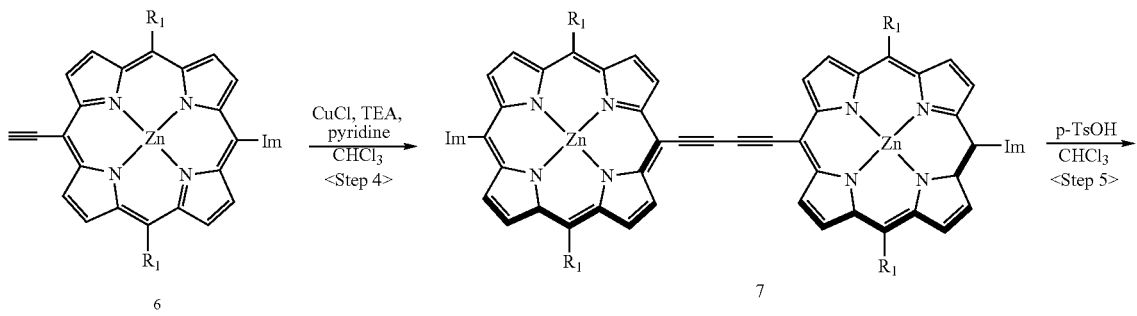
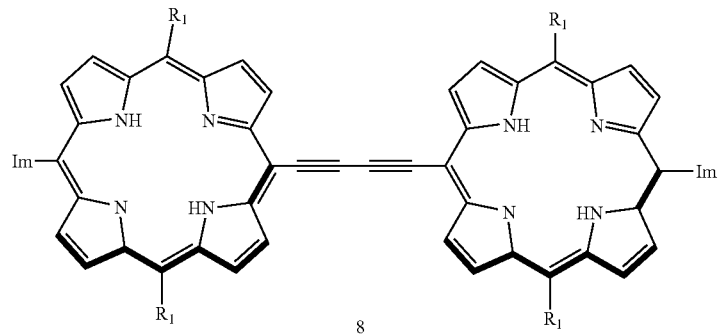

-continued
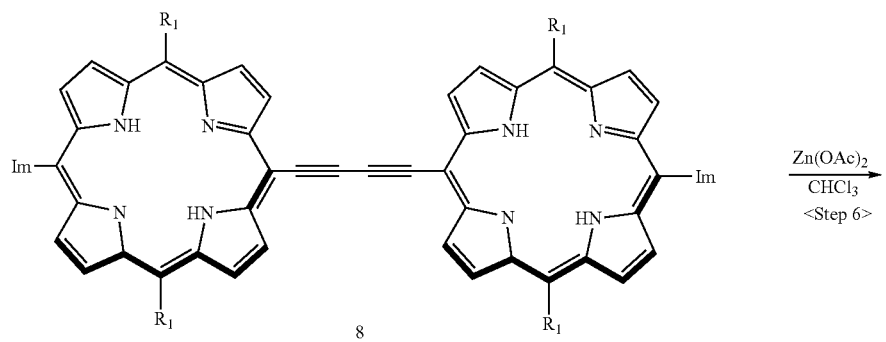
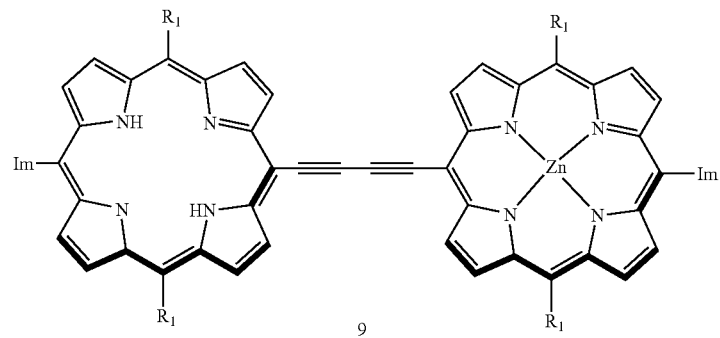
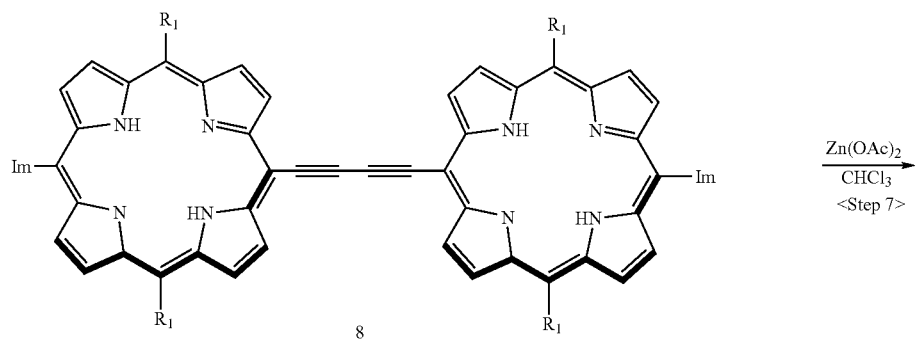
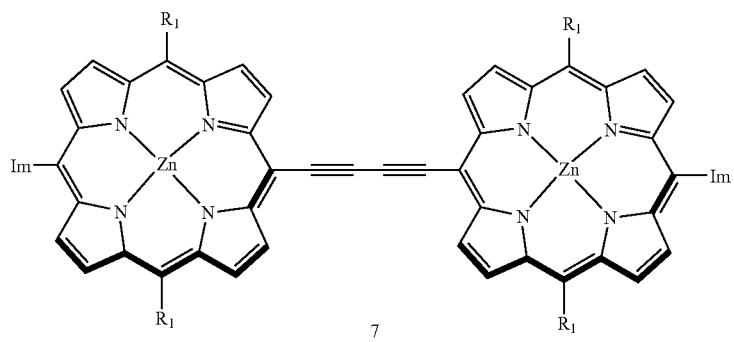

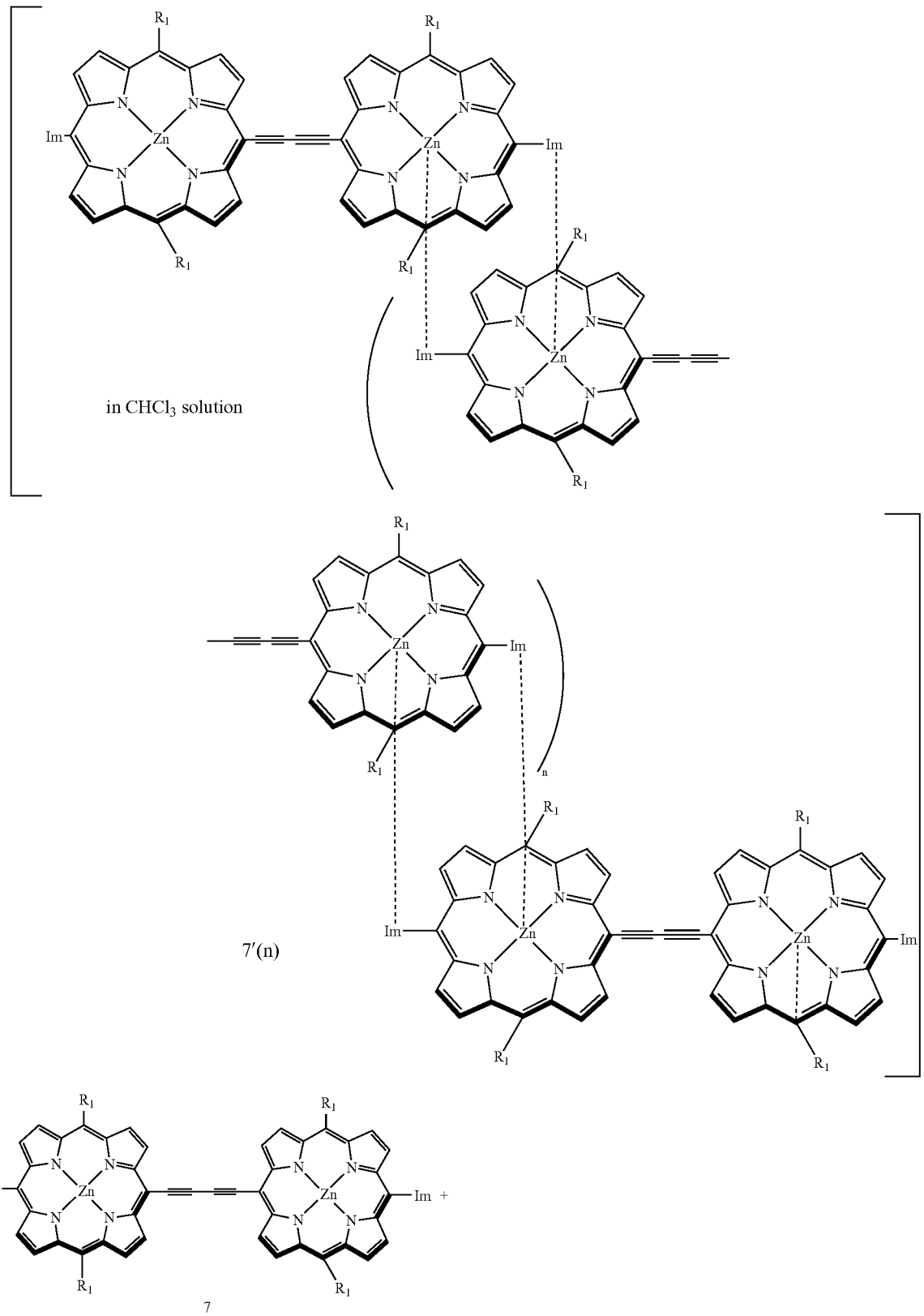
7'(n)
in CHCl₃ solution
7

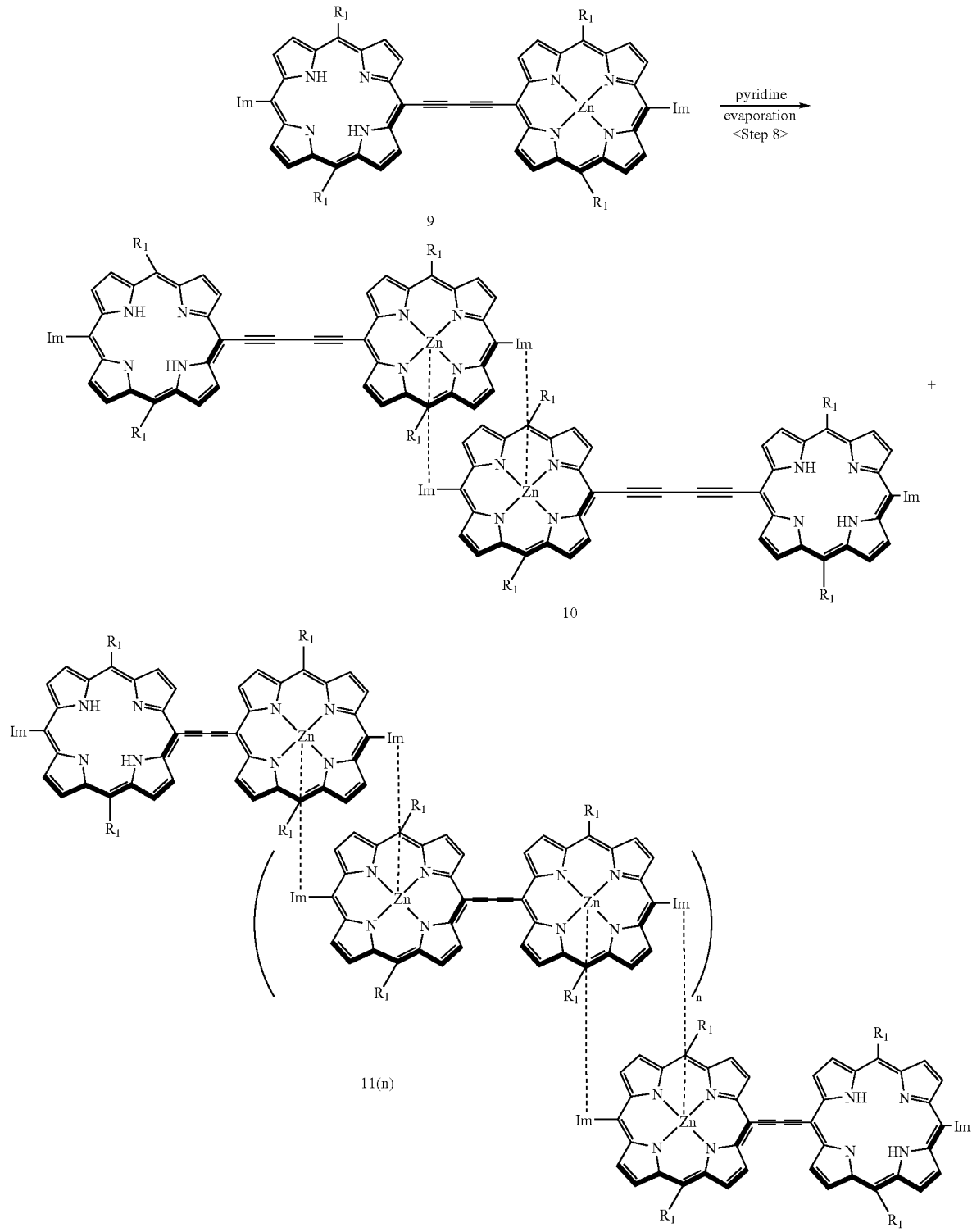

\<Step 1\> Synthesis of Compound 4

Compound 1 (wherein "TMS" represents trimethylsilyl group), compound 2, compound 3 (in the formulas mentioned above, $R_1$ and Im have the same meaning as defined in the formulas (1-1) and (1-2), the same can be applied to the other compounds in the following description) are dissolved in a solvent such as $CHCl_3$ or acetonitrile and the atmosphere thereof is substituted with nitrogen. Thereafter, TFA (trifluoroacetic acid) is added to the mixture to start the reaction. Chloranil (2,3,5,6-tetrachloro-p-benzoquinone) is then added to the mixture, whereby compound 4 is synthesized.

The ratio of the amounts to be added, of compound 1, compound 2 and compound 3, is generally set at 1:1:2 to 1:2:2.

The solvent may generally be used by the amount which is 500 to 5000 times as much as the amount of compound 2. The reaction temperature may generally be set in a range of 20 to 30° C. The reaction time may generally be set in a range of 30 to 300 minutes.

After the reaction is completed, processes such as purification may optionally be carried out, and then, the resulting substance is subjected to the next step, step 2. The purification process may be carried out after the reaction of step 1 is completed, for example, by adding an aqueous solution of sodium hydrogencarbonate to the resulting solution, then adding a solvent such as chloroform or dichloromethane thereto and separating the organic layer, concentrating the separated organic layer to dryness, and thereafter loading the obtained product on silica gel column chromatography.

<Step 2> Synthesis of Compound 5

Compound 4 obtained by the above-mentioned step 1 is converted into zinc complex 5. This reaction can be effected by dissolving compound 4 in a solvent such as chloroform or dichloromethane and adding zinc (II) acetate thereto.

The amount of zinc acetate to be added may generally be set at an amount which is 5 to 10,000 times as much as the amount of compound 4. The reaction temperature may generally be set at room temperature (in a range of around 25 to 30° C.). The reaction time may generally be set in a range of 0.5 to 3 hours.

After the reaction is completed, the reaction solution may be washed with distilled water and the organic layer is concentrated under reduced pressure, whereby compound 5 is obtained.

<Step 3> Synthesis of Compound 6

The TMS group of compound 5 obtained by the above-mentioned step 2 is removed. The removal of the TMS group can be effected by dissolving compound 5 in a solvent such as chloroform or dichloromethane, and adding TBAF (tetrabutylammonium fluoride) thereto.

The amount of TBAF to be added may generally be set at an amount which is 5 to 50 times as much as compound 5. The reaction temperature may generally be set at room temperature. The reaction time may generally be set in a range of 1 to 6 hours.

After the reaction is completed, the reaction solution is washed with distilled water and the organic layer is concentrated under reduced pressure. The residue, compound 6, is subjected to the next step, step 4, without being purified.

<Step 4 and Step 5> Synthesis of Compound 8

Compound 6 is dissolved in a solvent such as chloroform or dichloromethane. Pyridine is added to the mixture and then the mixture is stirred for 30 minutes. Thereafter, copper (I) chloride is added to and reacted with the mixture at room temperature.

The addition amounts of compound 6, pyridine and copper (I) chloride are generally set in ratios of 1:1.5:10 to 1:3:200. The reaction temperature may generally be set at a temperature in a range of 20 to 30° C. The reaction time may generally be set in a range of 1 to 30 hours.

After the reaction is completed, the reaction solution is washed with an aqueous ammonia solution or an aqueous ethylenediamine solution, and the solvent of the organic layer is evaporated off. The residue, compound 7, is dissolved in a solvent such as chloroform or dichloromethane, and p-TsOH (p-toluenesulfonic acid) is added thereto, thereby compound 8 is obtained.

The amount of p-TsOH to be added may generally be set at an amount of 2 to 100 times as much as compound 7. The reaction temperature may generally be set at room temperature. The reaction time may generally be set in a range of 0.5 to 1 hour.

After the reaction is completed, the reaction solution is washed with distilled water and an aqueous sodium hydrogencarbonate solution and then the organic layer is concentrated under reduced pressure. The residue is purified with gel permeation chromatography (GPC) and silica gel chromatography, whereby compound 8 is obtained.

<Step 6> Synthesis of Compound 9

One free base porphyrin of the bis(free base) porphyrins of compound 8 is converted into a zinc porphyrin. The conversion can be effected by dissolving compound 8 in a solvent such as chloroform or dichloromethane, and then adding zinc (II) acetate thereto.

The amount of zinc acetate to be added may generally be set at 1 to 2 times as much as compound 8. The reaction temperature may generally be set at room temperature. The reaction time may generally be set in a range of 0.5 to 3 hours.

After the reaction is completed, the reaction solution is washed with distilled water and then the organic layer is concentrated under reduced pressure. The resulting product is purified with GPC, whereby compound 9 is obtained. Compound 9 exist as compound 10 in chloroform.

<Step 7> Synthesis of Compound 7 from Compound 8

Both of the free base porphyrins of the bis(free base) porphyrin of compound 8 are converted into zinc porphyrins. The conversion can be effected by dissolving compound 8 in a solvent such as chloroform or dichloromethane, and then adding zinc (II) acetate thereto.

The amount of zinc acetate to be added may generally be set at 5 to 10,000 times as much as compound 8. The reaction temperature may generally be set at room temperature. The reaction time may generally be set in a range of 0.5 to 3 hours.

After the reaction is completed, the reaction solution is washed with distilled water and then the organic layer is concentrated under reduced pressure. Compound 7 is in the form of bis-acetylen-type poly(porphyrin) in chloroform (compound 7' (n)).

<Step 8> Synthesis of Porphyrin Arrays, Compound 10 and Compound 11 (n)

Compound 7 and compound 9 are dissolved in pyridine and mixed with each other. The reaction temperature may generally be set at room temperature. The reaction time may be set at 0.5 hours. The solvent is removed under reduced pressure.

The mixture of compound 10 and compound 11 (n) may be separated by subjecting the mixture to GPC, and using a solvent such as chloroform as an eluent.

Polystyrene may generally be employed as a stational phase in the column for purification with GPC.

The value of the repeating units (n) of compound 11 may be adjusted by changing the mixing ratio between compound 7 and compound 9. Specifically, the value of n of compound 11 is shifted to a larger value by increasing the mixing ratio of compound 7. Conversely, the value of n of compound 11 is shifted to a smaller value by increasing the mixing ratio of compound 9.

On the other hand, in the case of compound 7' (n) mentioned above, a non-polar solvent (such as chloroform, benzene and toluene) may be used in order to increase the value of n. Conversely, a polar solvent (such as methanol, ethanol and pyridine) may be used in order to decrease the value of n. A single solvent may be used, or a polar solvent and a non-polar solvent may be mixed in an appropriate manner, so that the polarity of the solvent as a whole can be adjusted as is desired.

Next, a method of preparing the covalent bond-fixed porphyrin array represented by the formula (4) of the present invention will be described by using an array wherein R is methyl, Im is 1-methyl-2-imidazolyl, $M_1=M_3$=zinc ion, $L_1$=(—C≡C—)$_2$, q=2, r=0 and a=H as an example. However, other covalent bond-fixed porphyrin arrays having different substituents may be synthesized in the similar manner as this.

The covalent bond-fixed porphyrin array represented by the formula (4) wherein R is methyl, Im is 1-methyl-2-imidazolyl, $M_1=M_3$=zinc ion, $L_1$=(—C≡C—)$_2$, q=2, r=0 and a=H may be synthesized via the steps shown in the following scheme 1, but the preparation method thereof is not limited to this.

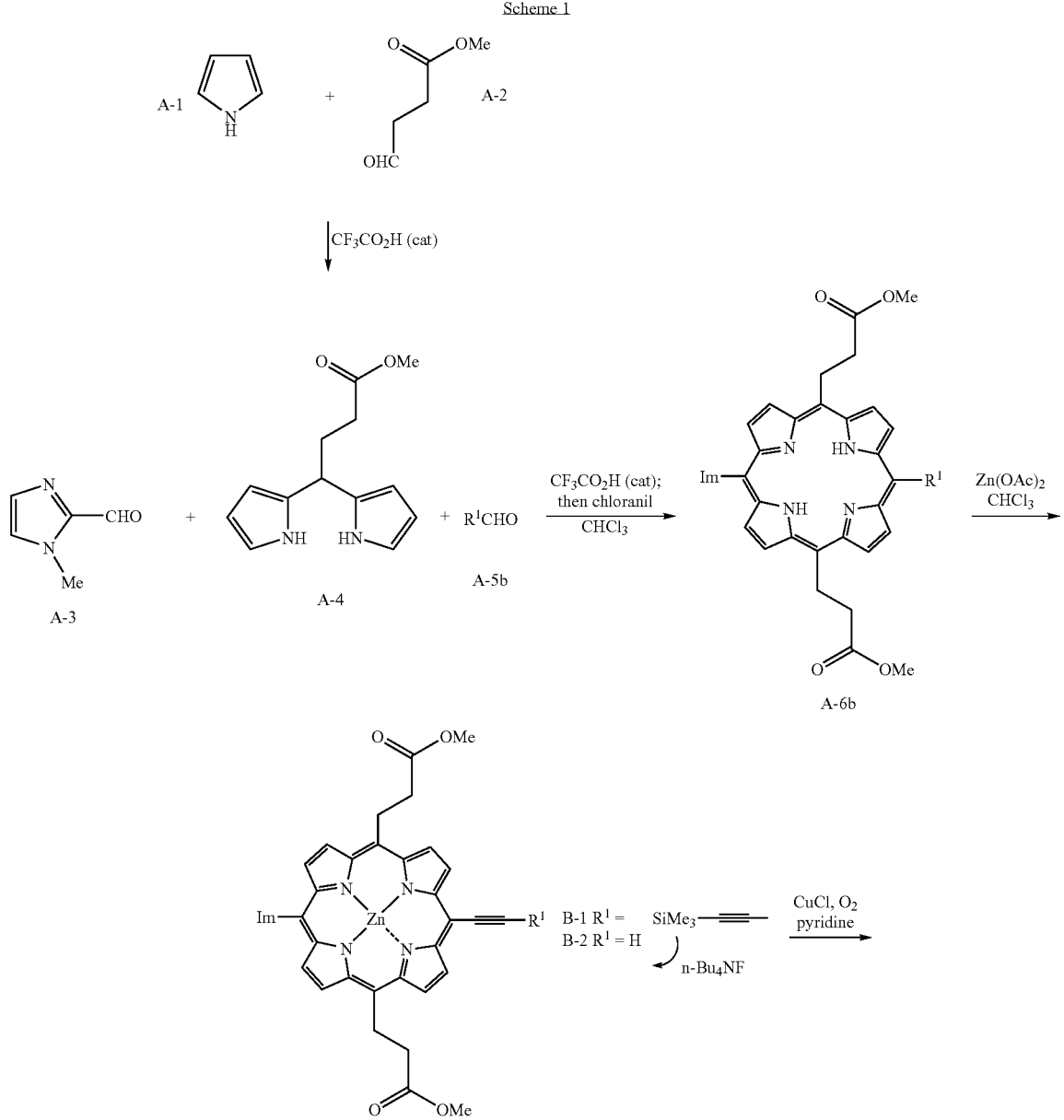

-continued
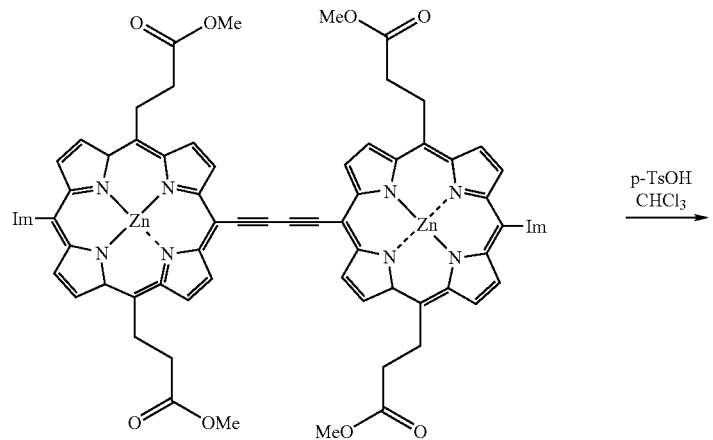
B-3
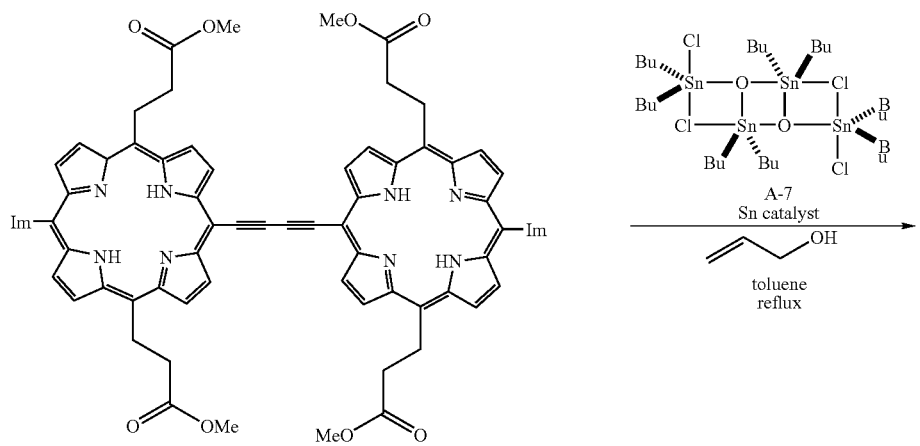
B-4
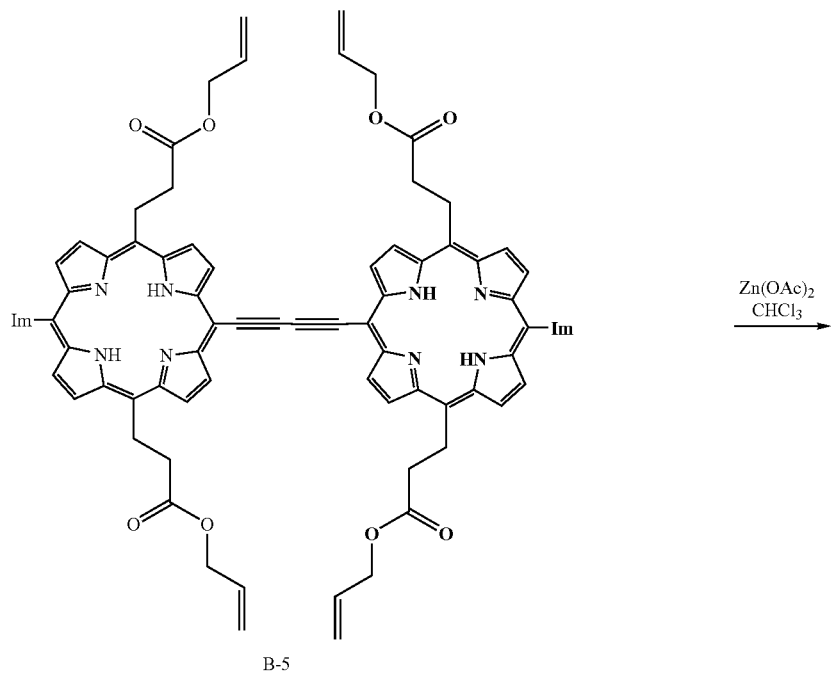
B-5

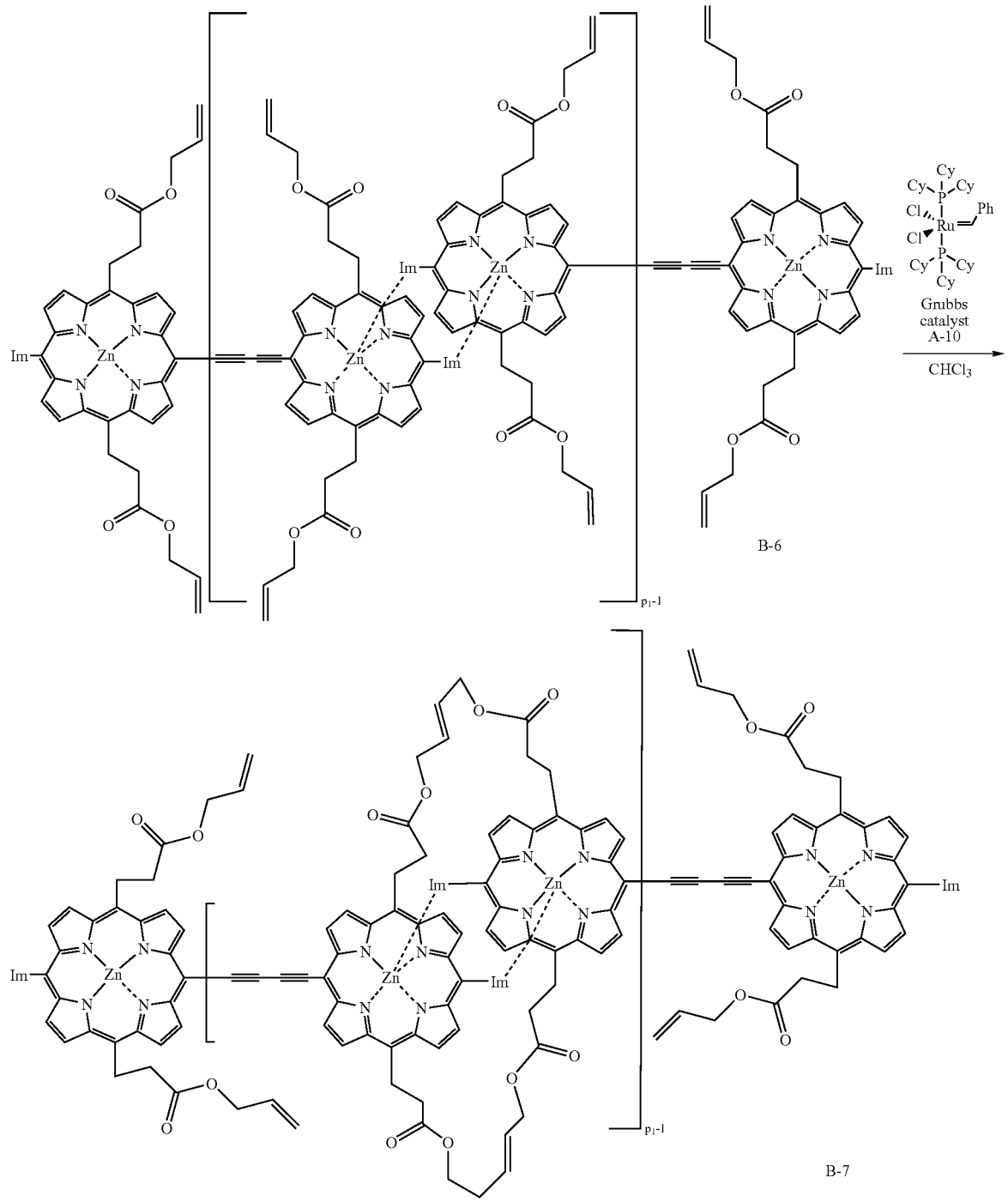

By the above method, a mixtures of compounds represented by the formula (4) having different degrees of polymerization represented by $p_1$-1 is obtained. The mixture may be separated into each component having a single degree of polymerization by gel filtration column chromatogram and the like. The degree of polymerization represented by $p_1$-1 may be adjusted by changing the amounts of the intermediate, compound B-5, and Grubbs catalyst, and the reaction time.

The "Grubbs catalyst" herein is a generic term for the ruthenium carbene complex developed by Grubbs et al., which is reactive in the olefin metathesis reaction. When this complex is used, even if an olefin compound having various functional groups such as ester, ketone and amide is employed as a reaction substance, the reaction selectively proceeds only with respect to the olefin sites (refer to the general theory of Grubbs et al. (T. M. Trnka, R. H. Grubbs, Acc. Chem. Res. 34, 18 (2001), the entire contents of which is incorporated herein by reference).

Further, the reaction starting from compound B-6 to compound B-7 in Scheme 1 is a reaction known as the cyclization metathesis reaction, which is described in detail in the aforementioned reference by Grubbs et al. The cyclization metathesis reaction is, in short, a reaction in which a compound having two alkenyl groups causes an olefin metathesis reaction to forms a cyclic compound.

The group represented by R of the both terminal porphyrins of compound B-6 and compound B-7 has the same meaning as defined for the substituent, R, in the formula (4). Typical examples of R include —CH=CH$_2$.

EXAMPLES

Example 1

An example of synthesizing the porphyrin arrays represented by the formulas (1-1) and (1-2) of the present invention will be described hereinafter. It should be noted that the method of synthesizing the porphyrin arrays of the present invention is not restricted to the present example.

1) Step 1

Synthesis of 5,15-bis(heptyl)-10-(trimethylsilyl-propargyl)-20-(1-methyl-2-imidazolyl)porphyrin (4)

1 g (4.1 mmol) of Meso-(n-heptyl)dipyromethane, 450 mg (4.1 mmol) of 1-methyl-2-formylimidozaole, 260 mg (2 mmol) of 1-trimethylsilylethynylaldehyde were added to 1 L of chloroform. The atmosphere of the reaction solution was substituted with N$_2$. Then, 1.2 mL (8.6 mmol) of trifluoroacetic acid was added to the reaction mixture. After the reaction mixture was stirred for 4 hours at room temperature, 1.6 g (6.5 mmol) of 2,3,5,6-tetrachloro-1,4-benzoquinone (chloranil) was added thereto. The reaction solution was then stirred for 3 hours. Thereafter, an aqueous solution of saturated sodium hydrogencarbonate was added to the mixture and the organic layer was extracted with chloroform. The extracted organic layer was dried with anhydrous sodium sulfate, and then the solvent was evaporated under reduced pressure. The obtained crude product was subjected to separation with silica gel chromatography (eluent: chloroform/acetone (9:1)), whereby 56 mg of the pure porphyrin 4 was obtained (the yield was 4%).

$^1$H NMR (600 MHz, CDCl$_3$) δ −2.71 (s, 2H; inner proton), 0.52 (s, 9H; TMS), 0.73 (t, J=7 Hz, 6H; C7), 1.14–1.16 (m, 8H; C6, C5), 1.29–1.34 (m, 4H; C4), 1.54 (quintet, 4H; C3), 2.20–2.22 (m, 4H; C2), 3.12 (s, 3H; NCH$_3$), 4.40–448 (m, 4H; C1), 7.30 (s, 1H; imidazole ring), 7.57 (s, 1H; imidazole ring), 8.20 (br, 2H, β), 8.91 (br, 2H, β), 9.16 (d, J=4 Hz, 2H, β), 9.55 (d, J=4 Hz, 2H, β); $^{13}$C NMR (150 MHz, CDCl$_3$) δ 0.50 (TMS), 14.2 (C7), 22.8 (C6), 29.4 (C4), 30.5 (C3), 32.0 (C5), 34.6 (NCH$_3$), 34.9 (C1), 38.7 (C2), 100.0 (TMS-C≡C—), 102.2 (meso), 107.5 (TMS-C≡C—), 114.8 (meso), 119.1 (meso), 121.4 (imidazole ring), 126.3 (imidazole), 127–131 (br, 4 carbons Porβ1-4)), 144–148 (br, 4 carbons (α1-4)), 148.2 (imidazole), Other 4 carbons (Porα) could not be observed by boarding.; UV (CHCl$_3$): 667 (Abs.; 0.0061), 608 (0.0028), 567 (0.0108), 528 (0.0072), 427 (0.1950) nm; Fluorescence (EX=427 nm, CHCl$_3$): 741, 670 nm; MALDI-TOF Mass C$_{43}$H$_{54}$N$_6$Si Calcd: 682.42; Found: 683.1 (M+H)$^+$.

2) Step 2

Synthesis of 5,15-bis(heptyl)-10-(trimethylsilyl-propargyl)-20-(1-methyl-2-imidazolyl)porphyrin zinc complex (5)

3 mL of a methanol solution of saturated zinc acetate was added to a chloroform solution (12 mL) of the porphyrin 4 (40 mg, 58.6 µmol). The reaction mixture was stirred for 1 hour at room temperature. Thereafter, water was added to the reaction mixture and the organic layer was extracted with chloroform. The extracted organic layer was dried with anhydrous sodium sulfate and then the solvent was evaporated under reduced pressure, whereby 44 mg of the pure porphyrin complex 5 was obtained (yield: 100%).

$^1$H NMR (600 MHz, CDCl$_3$) δ 0.73 (s, 9H; TMS), 1.00 (t, J=7 Hz, 6H; C7), 1.44–2.49 (m, 4H; C6, C5), 1.50–1.57 (m, 4H, C6, C5), 1.65 (s, 3H; NCH$_3$), 1.94–1.99 (m, 2H, C3), 2.04 (d, J=2 Hz, 1H; imidazole ring), 2.00–2.07 (m, 2H; C3), 2.70–2.74 (m, 2H; C2), 2.85–2.89 (m, 2H; C2), 4.96–5.09 (m, 4H, C1), 5.38 (d, J=4 Hz, 2H; Porβ), 5.47 (d, J=2 Hz, 1H; imidazole ring), 8.81 (d, J=4 Hz, 2H; Porβ), 9.61 (d, J=4 Hz, 2H; Porβ), 9.91 (d, J=4 Hz, 2H; Porβ); $^{13}$C NMR (150 MHz, CDCl$_3$) δ 0.7 (TMS), 14.3 (C7), 22.9 (C6), 29.8 (C4), 31.0 (C3), 32.3 (C5), 32.7 (NCH$_3$), 35.9 (C1), 39.5 (C2), 98.4 (meso), 99.0 (TMS-C≡C—), 99.7 (TMS-C≡C—), 109.7 (meso), 117.9 (imidazole ring), 118.9 (meso), 121.4 (imidazole ring), 127.3 (Porβ4), 129.0 (Porβ1), 129.3 (Porβ3), 131.3 (Porβ2), 145.5 (imidazole), 147.4 (Porα), 150.2 (Porα), 150.8 (Porα), 151.6 (Porα); UV (CHCl$_3$): 642 (Abs.; 0.0270), 577 (0.0090), 444 (0.1839), 425 (0.1136) nm; Fluorescence (EX=444 nm, CHCl$_3$): 704, 645 nm; MALDI-TOF Mass C$_{43}$H$_{52}$N$_6$SiZn Calcd: 744.33; Found: 745.2 (M+H)$^+$.

3) Step 3

Synthesis of 5,15-bis(heptyl)-10-ethynyl-20-(1-methyl-2-imidazolyl)porphyrin zinc complex (6)

1 M TBAF solution dissolved in THF (0.18 mL, the TBAF content being 0.18 mmol) was added to a chloroform solution (5 mL) of the porphyrin complex 5 (44 mg, 59 µmol) under a nitrogen atmosphere. The reaction mixture was stirred for 1 hour at room temperature. Thereafter, water was added to the reaction mixture and the organic layer was extracted with chloroform. The extracted organic layer was dried with anhydrous sodium sulfate and then the solvent was evaporated under reduced pressure, whereby 40 mg of the pure porphyrin complex 6 was obtained.

UV-vis (CHCl$_3$): 636 (Abs. 0.0806), 576 (0.0393), 440 (0.7057), 422 (0.4889) nm; Fluorescence (EX=440 nm, CHCl$_3$): 698, 640 nm; MALDI-TOF Mass C$_{40}$H$_{44}$N$_6$O$_4$Zn Calcd: 672.29; Found: 673.4 (M+H)$^+$.

4) Step 4 and Step 5

Synthesis of 1,3-bis(5-(15-(1-methyl-2-imidazolyl)-10,20-bis(heptyl)-porphyrinyl)) butadiyne (8)

1.9 g of copper (I) chloride (18.9 mmol) was added to a pyridine solution (20 mL) of porphyrin complex 6 (180 mg, 0.27 mmol), and oxygen was vigorously blown into the solution. The reaction mixture was stirred for 2 hours at room temperature and then washed with 25% aqueous solution of ammonia. The organic layer was extracted with chloroform. The extracted organic layer was dried with anhydrous sodium sulfate and then the solvent was evaporated under reduced pressure. The obtained crude product of the desired zinc complex 7 was dissolved in chloroform (10 mL), and p-toluenesulphonic acid•monohydrate (27 mmol) was added thereto. The reaction mixture was stirred for 1 hour at room temperature. Thereafter, an aqueous solution of saturated sodium hydrogencarbonate was added to the reaction solution to neutralize the reaction solution. The crude product was extracted with chloroform. The obtained crude product was purified with silica gel chromatography (eluent: chloroform/methanol (10:1)), whereby 50 mg of the desired product 8 was obtained at the yield of 15%.

UV-vis (CHCl$_3$): 715 (Abs. 0.0854), 609 (0.0648), 475 (0.2000), 444 (0.3149) nm; Fluorescence (EX=444 nm, CHCl$_3$): 800, 721 nm; MALDI-TOF Mass $C_{80}H_{90}N_{12}$ Calcd: 1218.74; Found: 1219.5 (M+H)$^+$.

5) Step 6

Synthesis of 1-(5-(15-(1-methyl-2-imidazolyl)-10,20-bis(heptyl)-zinc porphyrinyl)-3-(5'-(15'-(1-methyl-2-imidazolyl)-10',20'-bis(heptyl)-porphyrinyl)) butadiyne (9)

A methanol solution of zinc acetate (0.9 mg/0.5 mL, 4 μmol) was added to a chloroform solution (2 mL) of the bis-porphyrin 8 (5 mg, 4 μmol). The reaction mixture was stirred for 1 hour. Thereafter, water was added to the reaction mixture and the organic layer was extracted with chloroform. The extracted organic layer was dried with anhydrous sodium sulfate and then the solvent was evaporated under reduced pressure. The crude product was purified with silica gel column chromatography (eluent: chloroform/methanol (10:1)), whereby 5.5 mg of the desired product 9 was obtained with an equivalent amount. The porphyrin mono-complex 9 exists as a coordinated assembly 10 in chloroform.

UV-Vis (CHCl$_3$): 732 (Abs.; 0.3639), 660 (0.1328), 583 (0.1194), 484 (0.7188), 455 (0.6266), 429 (0.6525) nm; Fluorescence (EX=484 nm, CHCl$_3$): 840, 749 nm; MALDI-TOF Mass $C_{80}H_{88}N_{12}Zn_1$ Calcd: 1280.65; Found: 1281.7 (M+H)$^+$.

6) Step 7

Synthesis of 1,3-bis(5-(15-(1-methyl-2-imidazolyl)-10,20-bis(heptyl)-zinc porphyrinyl)) butadiyne (7)

3 mL of a methanol solution of saturated zinc acetate was added to a chloroform solution (3 mL) of the porphyrin 8 (10 mg, 8 μmol). The reaction mixture was stirred for 1 hour at room temperature. Thereafter, water was added to the reaction mixture and the organic layer was extracted with chloroform. The extracted organic layer was dried with anhydrous sodium sulfate and then the solvent was evaporated under reduced pressure, whereby 11 mg of the porphyrin complex 7 was obtained at the yield was 100%.

UV-Vis (CHCl$_3$): 732 (Abs.; 0.3639), 660 (0.1328), 583 (0.1194), 499 (0.7188), 455 (0.6266), 429 (0.6525) nm; Fluorescence (EX=484 nm, CHCl$_3$): 840, 749 nm; MALDI-TOF Mass $C_{80}H_{88}N_{12}Zn_2$ Calcd: 1348.65; Found: 1349.7 (M+H)$^+$.

7) Step 8

Synthesis of Porphyrin Array (11)

2.5 μmol of the porphyrin complex 7 and 7.7 μmol of the porphyrin mono-complex 9 were dissolved in 3 mL of pyridine. The mixture was stirred for 30 minutes at room temperature. The solvent was removed by a vacuum pump, whereby a mixture of the array 10 and the array 11 (n) were obtained.

Measurement Example 1

8) Measurement of Two-Photon Absorption Cross Section

The spectra of two-photon absorption of the arrays were measured in a chloroform solution, using the open aperture Z-scan method, with a Ti: sapphire pulse laser having a time resolution of 120 femtosecond. The wavelength was varied from 817 to 1282 nm by an optical parametric amplifier (OPA). The measurement was carried out using a 1 mm cell and scanning a distance of 60 mm fore and aft of the focus of the incident light (below 1 mW). No change was observed in the visible and ultraviolet absorption spectrum between before and after the Z-scan measurement. The value of the two-photon absorption cross section $\sigma^{(2)}$ was obtained from the following formula.

$$\sigma^{(2)} = \hbar\omega\beta/N \tag{1}$$

In the above-mentioned formula (1), ℏω represents photon energy, N represents the number density of molecules, β represents the two-photon absorption coefficient, satisfying the following formula.

$$q = \beta I_0 L \tag{2}$$

In the above-mentioned formula (2), the parameter q corresponds to the two-photon absorbance and can be obtained by performing "fitting" of the open aperture Z-scan curve with the theoretical equations (3) and (4) below. $I_0$ represents intensity of the incident light (IEEE. J. Quant. Electron. 26, 760, (1990), Handbook of Nonlinear Optics, Marcel Dekker, New York (1996)).

$$T(\zeta) = \frac{(1-R)^2 e^{(-\alpha^{(1)}L)}}{\sqrt{\pi}\, q(\zeta)} \int_{-\infty}^{\infty} \ln[1 + q(\zeta)e^{(-x^2)}]dx \tag{3}$$

$$q(\zeta) = \frac{q}{1+\zeta^2} \tag{4}$$

Equation (3) describes the normalized transmittance of a sample that exhibits only two-photon absorption as nonlinear absorption for a Gaussian-pulsed Gaussian beam, where ζ is the normalized z-position defined as $\zeta = (z-z_0)/z_R$ and $z_0$ and $z_R$ are the focal position and the Rayleigh range, respectively. T(ζ) is normalized to unity at a position far from the focal position, i.e., T(ζ→±∞)=1. $\alpha^{(1)}$ is the linear (one-photon) absorption coefficient, R is Fresnel reflectance at the curvette cell walls, and L denotes the path length of the sample.

FIG. 1 shows the two-photon absorption spectrum of the array 10 and that of reference array 12 measured by the above-mentioned method. Another, smaller graph marked by the black arrow in FIG. 1 shows the spectrum of reference array 12 which has been enlarged in the direction of the vertical axis thereof. The structures of the array 10 and reference array 12 are shown below.

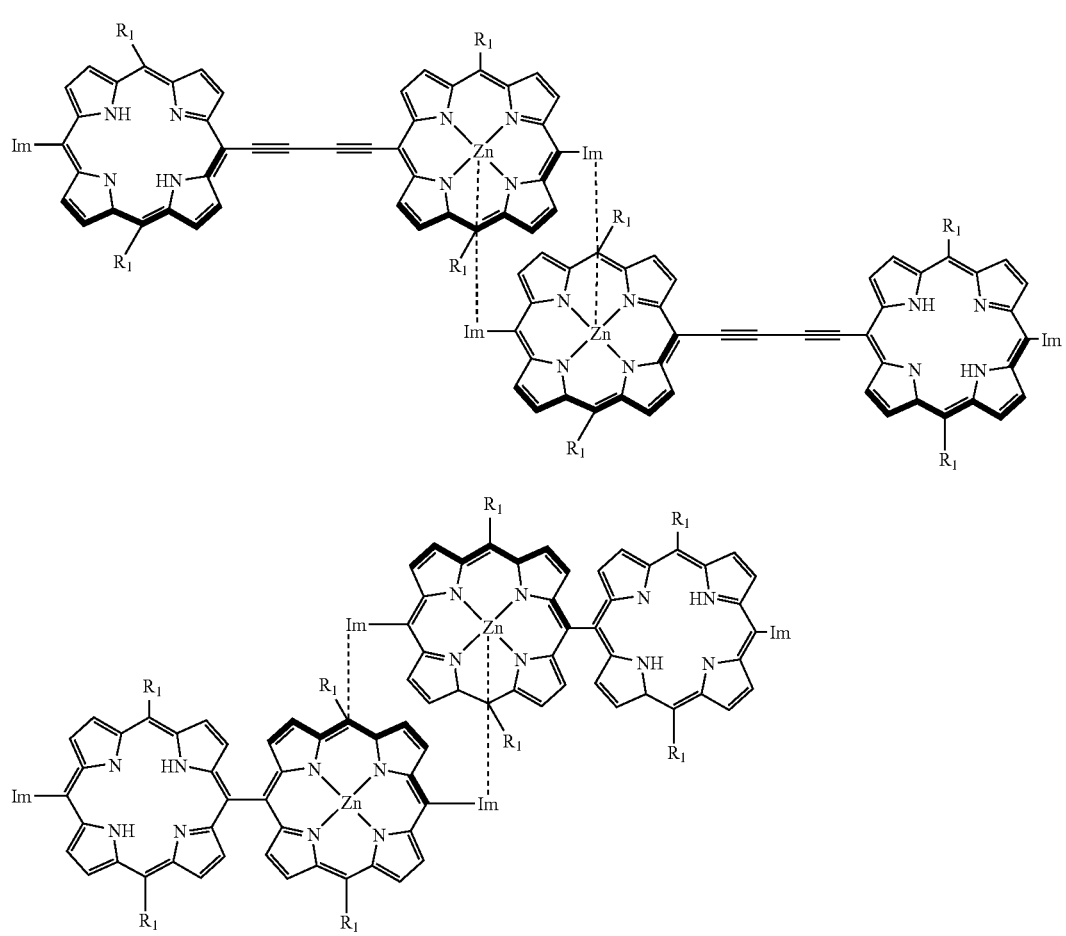

(wherein $R_1$=n-heptyl and Im=1-methyl-2-imidazolyl).

The method of synthesizing reference array 12 has already been reported (J. Am. Chem. Soc., 124, 22–23 (2002)). Reference array 12 includes meso-type dimer of mono-zinc complexes, and is in an assembled structure formed by coordinate bonds, in chloroform, as shown in FIG. 1.

The vertical axis of the spectra represents two-photon absorption cross section $\sigma^{(2)}$, and the unit thereof, i.e., 1 GM, corresponds to $1\times10^{-50}$ cm$^4$ s photon$^{-1}$. The maximum value of the two-photon absorption cross section of the reference array 12, which is of meso-type, was 370 GM (at 964 nm). On the contrary, the maximum value of the two-photon absorption section of the array 10, which was of bis-acetylen-type, was 7600 GM (at 887 nm), which was approximately 20 times as much as the maximum value of the two-photon absorption cross section of the reference array 12. It is assumed that the conjugation system between the porphyrins of the bis-acetylen-type is expanded and thus the molecular polarization therein due to the absorption of the first photon becomes larger than that observed in the meso-type, whereby the transition probability of the absorption of the second photon, of the bis-acetylen-type, is increased, as compared with the meso-type.

In the measurement using a femtosecond laser, there have been very few reports in which the maximum value of the two-photon absorption cross section reached 1000 GM. In 2002, Drobizhev et al. reported that octanitrophenyltetraazaporphyrin having nitrophenyl groups as acceptors exhibits 1600 GM (at 770 nm, 150 fs) (Chem. Phys. Lett., 361, 504–512 (2002)). However, it is generally difficult, in terms of organic synthesis, to introduce an acceptor by a covalent bond. Conversely, in the present invention, coordinate bonds are used and thus, an acceptor/donor can be easily introduced to the porphyrin array. It has been discovered by using ultrafast femtosecond laser that the porphyrin array of the present invention exhibits large two-photon absorption.

The two-photon absorption cross sections of the porphyrin array 10 of the invention and reference array 12 are summarized in Table 1 below.

TABLE 1

| Sample | $\sigma(2)$ /GM | $\sigma(2)$ /GM (per porphyrin) | Wavelength/ nm |
|---|---|---|---|
| 10 | 7600 | 1900 | 887 |
| 12 | 370 | 91 | 964 |

Example 2

A synthesis example of the porphyrin array represented by the formula (4) of the present invention will be described below, but the synthesis method thereof is not limited to this.

Meso-(methoxycarbonylethyl) dipyrromethane (A-4)

Meso-(methoxycarbonylethyl) dipyrromethane (A-4) was synthesized by stirring methoxycarbonyl propanal (11.6 g, 0.1 mol) and pyrrole (280 mL, 4 mol) in the presence of trifluoroacetic acid (1.4 mL, 10 mmol), in a method similar to that described in the reference (Y. Tomohiro, A. Satake, Y. Kobuke, J. Org. Chem. 2001, 66, 8442–8446). The resulting product was purified with silica gel chromatography (eluent: hexane/EtOAc (5:1)), whereby 17 g (73%) of meso-(methoxycarbonylethyl) dipyrromethane (A-4) was obtained.

$^1$H NMR (600 MHz, CDCl$_3$) δ 2.22–2.26 (m, 2H), 2.29–2.33 (m, 2H), 3.63 (s, 3H), 3.99 (t, J=7.2 Hz, 1H), 6.05–6.07 (m, 2H, pyH4), 6.12–6.14 (m, 2H, pyH5), 6.58–6.62 (m, 2H, pyH2), 7.78 (br, 2H, NH); $^{13}$C NMR (150 MHz, CDCl$_3$) δ 29.5, 31.9, 36.9, 51.6, 105.8, 108.1, 117.3, 132.4, 174.0.

Sn Catalyst A-7

Sn catalyst A-7 was synthesized according to the method of Otera et al. and used for the present example (Junzo Otera, Nobuhisa Dan-oh, Hitosi Nozaki, J. Org. Chem. 1991, 56, 5307–5311).

Grubbs Catalyst A-10

Fluka 09587 (manufactured by Fluka Co., Ltd.) (Benzylidene-bis(tricyclohexylphosphine)-dichlororuthenium) was purchased from WAKENYAKU Co., Ltd, and used for the present example. 5,15-Bis(methoxycarbonylethyl)-10-(1'-trimethylsilylethynyl)-20-(1''-methyl-2''-imidazolyl)porphyrin (A-6b)

This compound was prepared by adding meso-(methoxycarbonylethyl)dipyrromethane A-4 (3 g, 13 mmol), 1-methyl-2-formyl-imidazole A-3 (1.4 g, 13 mmol), 1-trimethylsilyl-ethynylaldehyde A-5b (0.8 g, 6.5 mmol), trifluoroacetic acid (3.7 mL, 26 mmol) and chloranil (4.8 g, 20 mmol), to deoxygenated chloroform (3 L). The thus obtained crude product was loaded on a silica gel column chromatography (eluent: chloroform/MeOH (9:1)) to give A-6b (120 mg, 3%).

$^1$H NMR (600 MHz, CDCl$_3$) δ −2.78 (s, 2H; inner proton), 0.67 (s, 9H; TMS), 3.33 (s, 3H; NCH$_3$), 3.43 (t, J=7.2 Hz, 4H; ester β), 3.7 (s, 6H; COOMe), 5.17–5.19 (m, 4H; ester α), 7.46 (br.s, 1H; imidazole ring), 7.70 (br.s, 1H; imidazole ring), 8.71 (d, J=4.2 Hz, 2H; Porβ), 9.34 (d, J=4.2 Hz, 2H; Porβ), 9.41 (d, J=4.2 Hz, 2H; Porβ), 9.70 (d, J=4.2 Hz, 2H; Porβ); $^{13}$C NMR (150 MHz, CDCl$_3$) δ 0.4 (TMS), 30.2 (ester α), 34.6 (NCH$_3$), 41.7 (ester β), 52.0 (COOMe), 100.1 (TMS-C≡C—), 102.5 (meso), 106.4 (meso), 107.1 (TMS-C≡C—), 118.3 (meso), 121.7 (imidazole ring), 128.2 (Porβ), 128.3 (imidazole ring), 128.4 (Porβ), 131.2 (Porβ), 131.9 (Porβ), 144–147 (br, 4 carbons (Porα)), 148.4 (Im N—C=N), 173.0 (C=O); UV-Vis (CHCl$_3$): 665 (Abs.; 0.0651), 608 (0.0553), 566 (0.1405), 527 (0.1086), 427 (2.3982) nm; Fluorescence (EX=427 nm, CHCl$_3$): 740, 668 nm; MALDI-TOF MASS C$_{37}$H$_{38}$N$_6$O$_4$Si Calcd: 658.27; Found: 659.2 (M+H)$^+$.

5,15-Bis(methoxycarbonylethyl)-10-(1'-trimethylsilylethynyl)-20-(1''-methyl-2''-imidazolyl)porphyrinatozinc (B-1)

To a chloroform solution (15 mL) of porphyrin A-6b (120 mg, 0.18 mmol), a methanol solution (5 mL) of saturated zinc acetate was added. After stirring the mixture for 1 hour at room temperature, water was added to the reaction solution, and the organic layer was extracted with chloroform. The extracted organic layer was dried with anhydrous sodium sulfate, and the solvent was evaporated under reduced pressure, thereby 130 mg of B-1 was obtained.

$^1$H NMR (600 MHz, CDCl$_3$) δ 0.74 (s, 9H; TMS), 1.65 (s, 3H; NCH$_3$), 1.98 (br.s, 1H; imidazole ring), 3.64–3.81 (m, 4H; ester β), 3.89 (s, 6H; COOMe), 5.42–5.53 (m, 7H; ester α & imidazole ring & Porβ4), 8.86 (d, J=5 Hz, 2H; Porβ3), 9.66 (d, J=5 Hz, 2H; Porβ1), 9.93 (d, J=5 Hz, 2H; Porβ2); $^{13}$C NMR (150 MHz, CDCl$_3$) δ 0.7 (TMS), 31.0 (ester α), 32.7 (NCH$_3$), 42.5 (ester β), 52.1 (COOMe), 98.7 (meso), 99.8 (TMS-C≡C—), 100.4 (TMS-C≡C—), 109.2 (meso), 118.4 (imidazole ring), 118.5 (meso), 121.9 (imidazole ring), 127.9 (Porβ4), 128.8 (Porβ1), 129.3 (Porβ3), 131.9 (Porβ2), 145.5 (Im N—C=N), 147.7 (Porα), 150.0 (Porα), 150.5 (Porα), 152.0 (Porα), 172.6 (C=O).

5,15-Bis(methoxycarbonylethyl)-10-(ethynyl)-20-(1'-methyl-2'-imidazolyl)porphyrinatozinc (B-2)

To a chloroform solution (15 mL) of porphyrin B-1 (130 mg, 0.18 mmol), 1M THF solution of tetrabutylammonium fluoride (0.6 mL) was added. After stirring the mixture for 30 min at room temperature, water was added to the reaction solution, and the organic layer was extracted with chloroform. The extracted organic layer was dried with anhydrous sodium sulfate, and the solvent was evaporated under reduced pressure, thereby 117 mg of B-2 was obtained $^1$H NMR (600 MHz, CDCl$_3$) δ 1.66 (s, 3H; NCH$_3$), 2.0 (d, J=1.2 Hz, 1H; imidazole ring), 3.61–3.82 (m, 4H; ester β), 3.90 (s, 6H; COOMe), 5.42–5.45 (m, 4H; ester α), 5.45 (d, J=4.2 Hz, 2H; Porβ4), 5.55 (d, J=1.2 Hz, 1H; imidazole ring), 8.87 (d, J=4.2 Hz, 2H; Porβ3), 9.67 (d, J=4.2 Hz, 2H; Porβ1), 9.95 (d, J=4.2 Hz, 2H; Porβ2); UV (CHCl$_3$): 632 (Abs. 0.0125), 576 (0.0087), 440 (0.1280), 422 (0.0874) nm; Fluorescence (EX=440 nm, CHCl$_3$): 694, 634, (EX=422 nm, CHCl$_3$): 691, 635 nm; MALDI-TOF Mass C$_{34}$H$_{28}$N$_6$O$_4$Zn Calcd: 648.15; Found: 649.12 (M+H)$^+$.

1,4-Bis[10{5',15'-Bis(methoxycarbonylethyl)-20'-(1''-methyl-2''-imidazolyl)porphyrinyl}]ethan-1,3-diyne (B-4)

Cuprous chloride (89 mg) was added to porphyrin B-2 (117 mg, 0.18 mmol) in pyridine (20 mL). The reaction solution was stirred for 1 hour at room temperature under oxygen gas bubbling. Thereafter, water was added to the reaction solution, and extracted with chloroform. The extracted organic layer was washed with a saturated EDTA (ethylenediamine tetraacetic acid) aqueous solution and dried over anhydrous sodium sulfate, and then the solvent was evaporated under reduced pressure. An excessive amount of p-toluenesulphonic acid monohydrate was added to a chloroform solution (10 mL) of the thus obtained crude product, and the mixture was stirred for 1 hour. Thereafter, an aqueous solution of saturated sodium hydrogencarbonate was added to the mixture. The organic layer was extracted with chloroform. The extracted organic layer was dried over anhydrous sodium sulfate, and then the solvent was evaporated under reduced pressure. The thus obtained crude product was loaded on a silica gel column (eluent: chloroform/methanol (9:1)) to give B-4 (84 mg, 40%). MALDI-TOF MASS C$_{68}$H$_{58}$N$_{12}$O$_8$ Calcd: 1170.45; Found: 1171.33 (M+H)$^+$.

1,4-Bis[10{5',15'-Bis(allyloxycarbonylethyl)-20'-(1"-methyl-2"-imidazolyl)porphyrinyl}]ethan-1,3-diyne (B-5)

Porphyrin B-4 (80 mg, 68 μmol) and allyl alcohol (93 μL, 1.4 mmol) in toluene (1 mL) was stirred under $N_2$ atmosphere. Thereafter, the Sn catalyst A-7 (1 mg, 2 μmol) was added to the solution, and solution was refluxed for 4 hr at 120° C. The completion of the reaction was checked with MALDI-TOF MASS. Thereafter, water was added to the reaction solution, and extracted the organic layer with chloroform. The extracted organic layer was dried over anhydrous sodium sulfate and then the solvent was evaporated under reduced pressure to obtain crude product. The thus obtained crude product was loaded on a silica gel chromatography (eluent: chloroform/methanol (10:1)), to give pure B-5 (64 mg, 80%).

$^1$H NMR (600 MHz, CDCl$_3$) δ −2.82 (s, 4H; inner proton), 3.34 (br.s, 6H; NCH$_3$), 3.42–3.48 (m, 8H; ester β), 4.68–4.71 (m, 8H; O—CH$_2$—C≡C), 4.94–5.08 (m, 8H; ester α), 5.23 (br.d, J=7.2 Hz, 4H; —C=CH$_2$), 5.34 (br.d, J=16.2 Hz, 4H; —C=CH$_2$), 5.90–5.98 (m, 4H; —CH=C), 7.52 (br, 2H; imidazole ring), 7.77 (br, 2H; imidazole ring), 8.72 (br, 4H; Porβ), 9.31 (br, 8H; β), 9.89 (br, 4H; Porβ); $^{13}$C NMR (150 MHz, CDCl$_3$) δ 30.5 (ester α), 34.6 (NCH$_3$), 41.8 (ester β), 65.6 (O—C—C≡C), 118.6 (O—C—C≡C), 121.6 (imdazole ring), 128.5 (Porβ), 128.9 (imidazole ring), 131.4 (Porβ), 132.1 (O—C—C≡C), 144.5–148.2 (br, 4 carbons (Porα)), 148.3 (Im N—C=N), 172.2 (C=O); UV-Vis (CHCl$_3$): 709 (Abs.; 0.0537), 608 (0.0500), 474 (0.1542), 445 (0.2224), 433 (0.2186), 415 (0.2085) nm; Fluorescence (EX=474 nm, CHCl$_3$): 789, 715 nm; MALDI-TOF MASS C$_{76}$H$_{66}$N$_{12}$O$_8$ Calcd: 1274.51; Found: 1275.01 (M+H)$^+$.

Zn form of B-5 (B-6)

Saturated zinc acetate solution in methanol (1 mL) was added to porphyrin B-5 (64 mg, 50 μmol) in chloroform (3 mL). The mixture was stirred for 1 hour at room temperature, water was added to the reaction solution, then the organic layer was extracted with chloroform. The extracted organic layer was dried over anhydrous sodium sulfate and then the solvent was evaporated under reduced pressure to give B-6 (70 mg).

UV (CHCl$_3$): 731 (Abs.; 0.0161), 669 (0.0063), 582 (0.0036), 501 (0.0296), 462 (0.0188), 429 (0.0171) nm; Fluorescence (EX=501 nm, CHCl$_3$): 817, 740 nm; MALDI-TOF MASS C$_{76}$H$_{62}$N$_{12}$O$_8$Zn$_2$ Calcd: 1398.34; Found: 1399.21 (M+H)$^+$.

B-7

Figure 2:
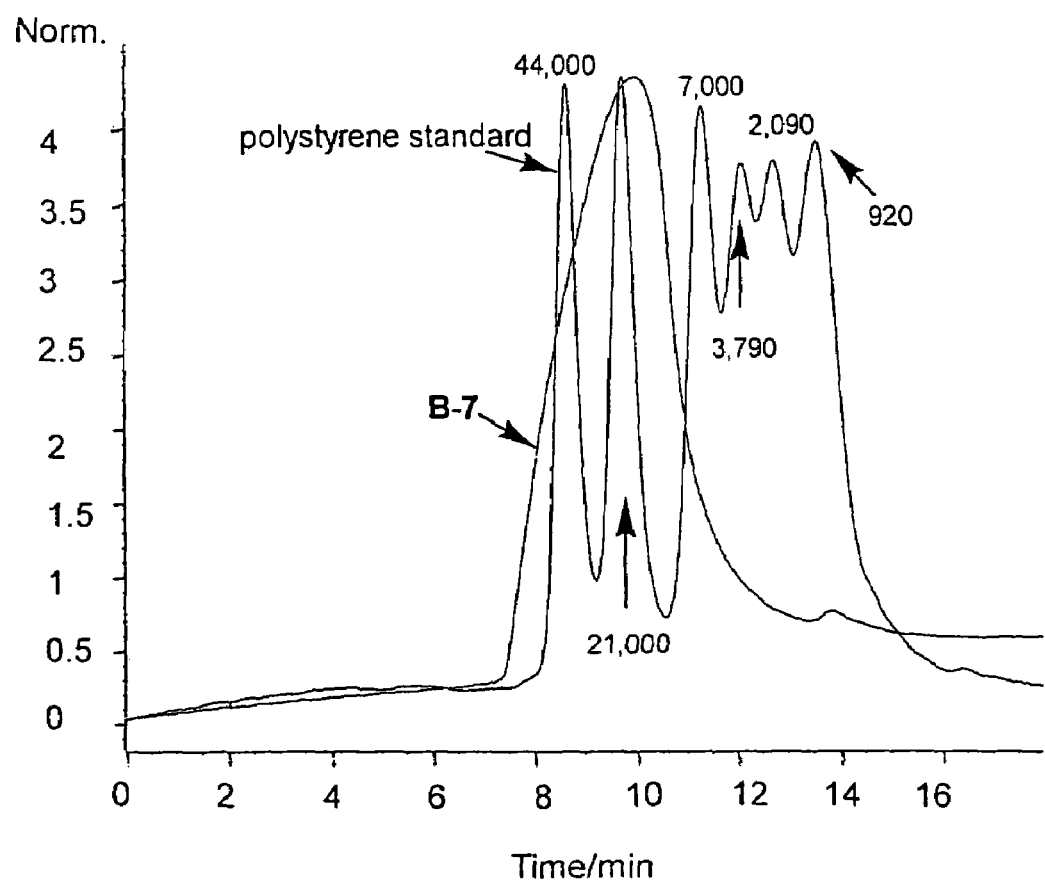
FIG. 2 is gel filtration column chromatogram of the polymer B-7.
Figure 3:
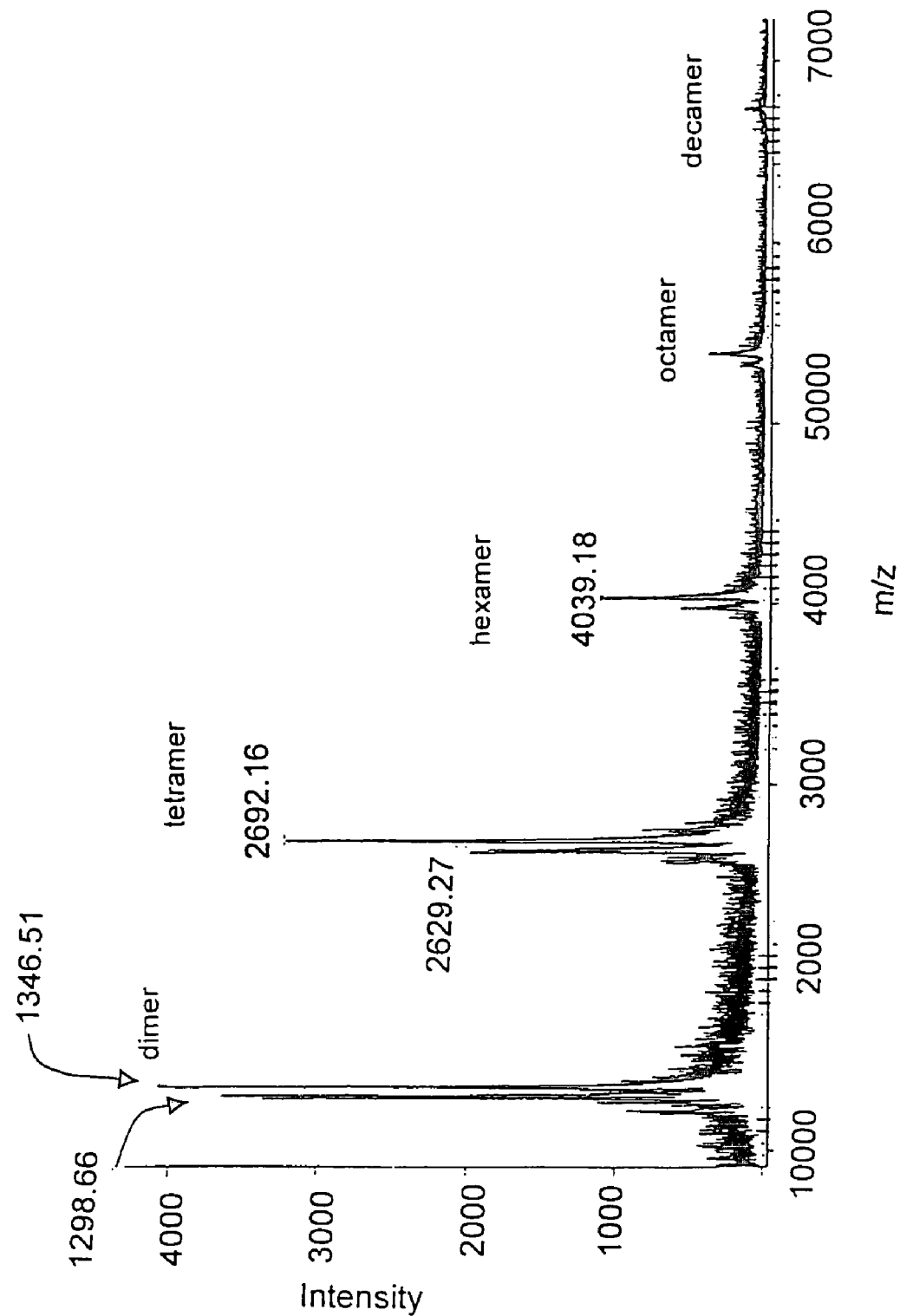
FIG. 3 is MALDI-TOF mass spectrometry of the polymer B-7.

Zinc porphyrin B-6 (70 mg, 50 μmol) in chloroform (2 mL) was stirred under $N_2$ atmosphere. Thereafter, the ruthenium carbene complex (1 mg, 10 μmol) was added to the solution. The reaction solution was stirred for 3 hours at room temperature, water was added to the reaction solution, and then the organic layer was extracted with chloroform. The organic layer was dried over anhydrous sodium sulfate and then the solvent was evaporated under reduced pressure. The thus obtained crude product was loaded on gel column chromatography (eluent: chloroform/methanol (9:1)) to give B-7 (54 mg) fixed with covalent bonds. The obtained B-7 was analyzed by using a size exclusion column chromatography (JAIGEL-2.5HA), and the chromatogram shown in FIG. 2 was obtained. As a result of comparison with the polystyrene reference substance, it was confirmed that a polymer which exhibits the distribution maximum of the molecular weight thereof in the vicinity of 20,000 had been generated. The result of the MALDI-TOF MASS spectrometry of B-7 is shown in FIG. 3. In the compound B-7, the carbon-carbon bond cleavage reaction occurs at the bis-acetylenic site thereof during the measurement of mass spectroscopy, and thus peaks are observed at the molecular weights which correspond to multiples of the porphyrin unit. The largest value of the molecular weights indicated by these peaks reaches or exceed 6000. The peak in the vicinity of the molecular weight of 6742 corresponds to the porphyrin decamer. On the contrary, no peaks which correspond to the fragments whose molecular weight is 2000 or more were observed in the compound B-6 which had not been subjected to the fixation. From these results, it is apparent that stability of the polymer has been significantly enhanced by the fixation. Further, from the measurement result of ultraviolet-visible absorption spectrum of the compound B-7 in pyridine, it was confirmed that the assembled structure of the compound was maintained.

Figure 4:
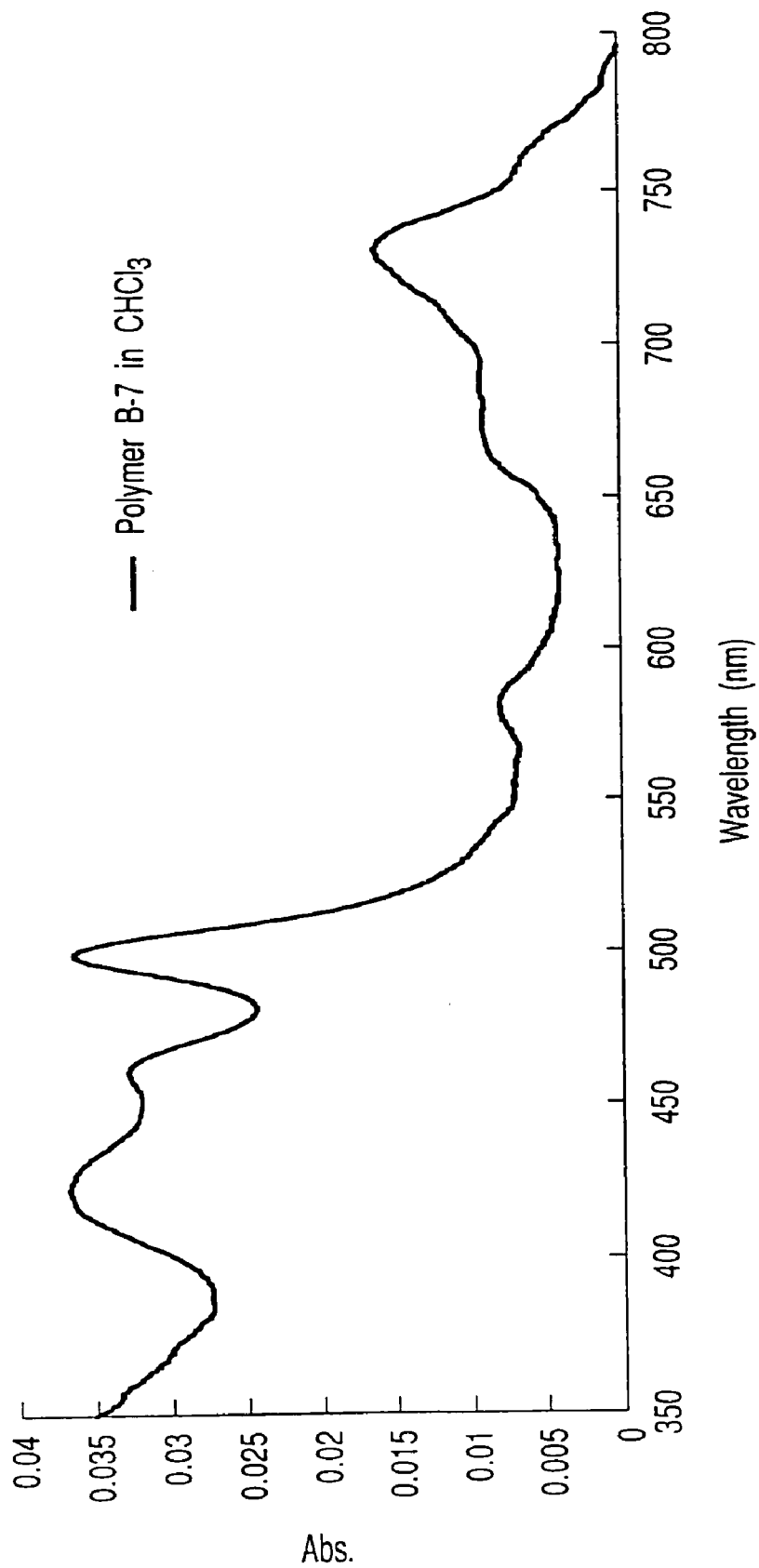
FIG. 4 is ultraviolet and visible region absorption spectrum of polymer B-7 (in chloroform).
Figure 5:
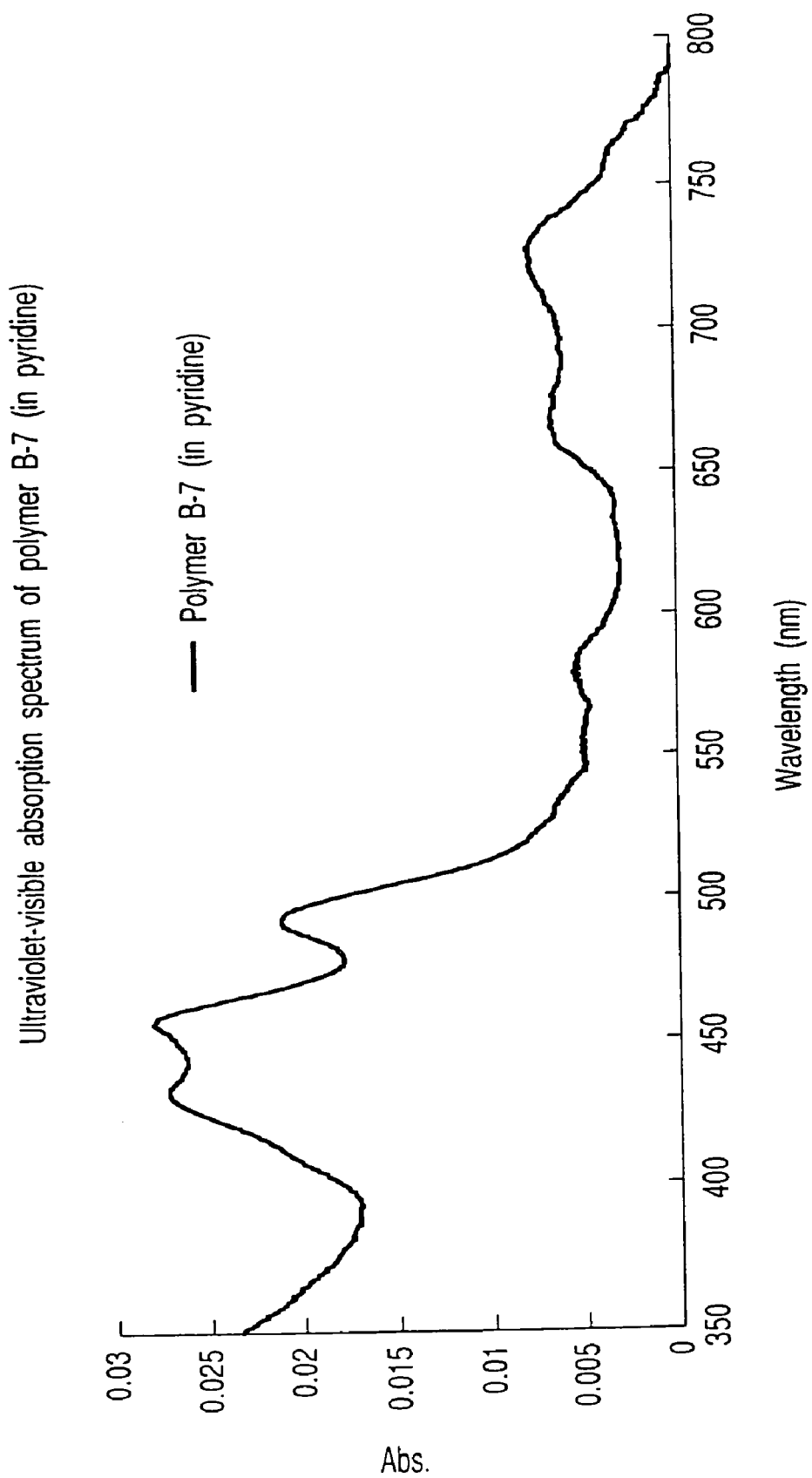
FIG. 5 is a view of ultraviolet and visible range absorption spectrum of polymer B-7 (in pyridine).
Figure 6:
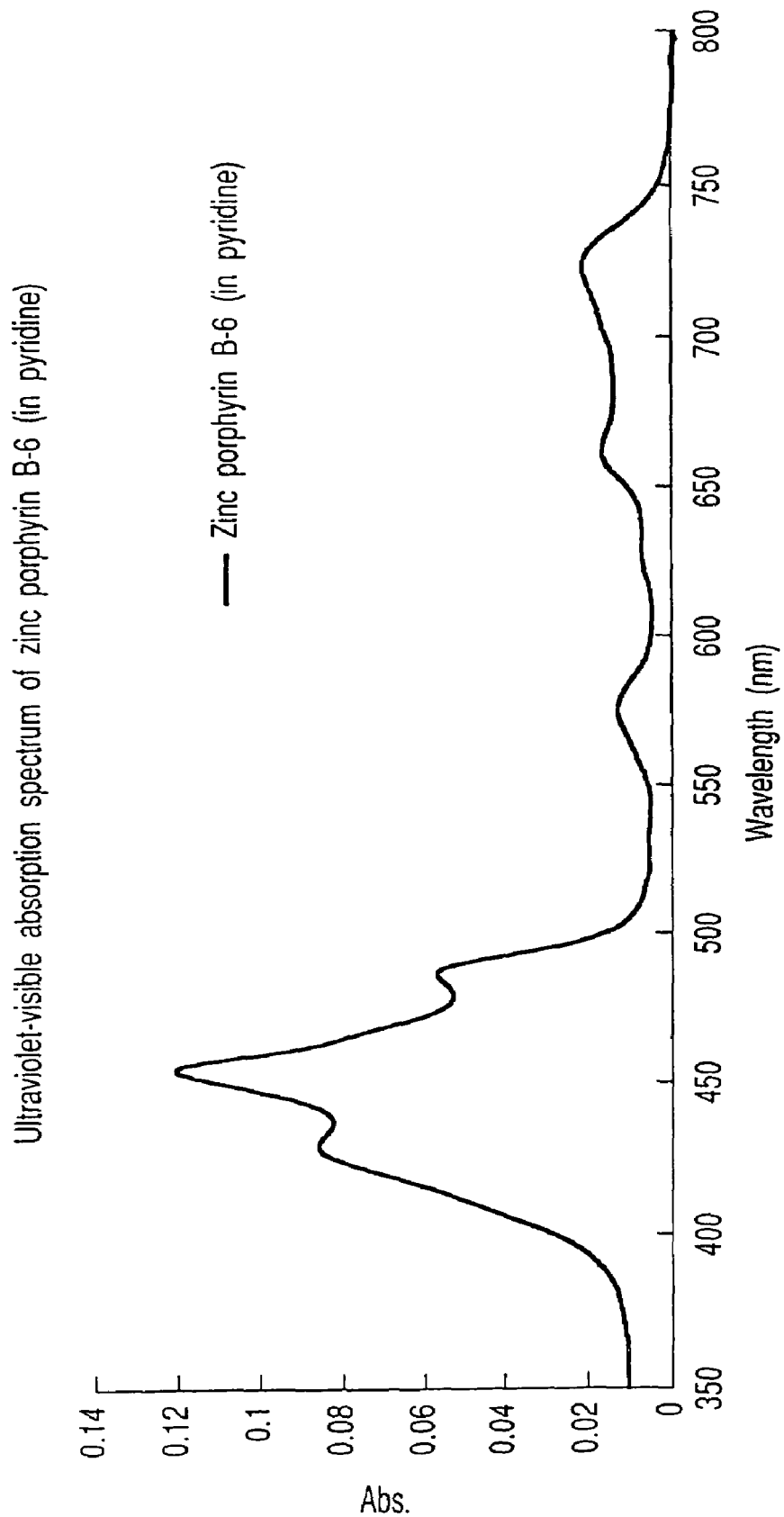
FIG. 6 is a view of ultraviolet and visible range absorption spectrum of zinc porphyrin polymer B-6 (in pyridine).

FIG. 4 shows the ultraviolet-visible absorption spectrum (UV-Vis spectrum), in chloroform, of the polymer B-7 which has been subjected to fixation. FIG. 5 shows the ultraviolet-visible absorption spectrum, in pyridine, of the polymer B-7 which has been subjected to fixation. FIG. 6 shows the ultraviolet-visible absorption spectrum (UV-Vis spectrum), in pyridine, of the polymer B-6 which has not been subjected to the fixation. The data of zinc porphyrin B-6 which has not been subjected to the fixation shows that B-6 is completely dissociated to monomers in pyridine, and the large absorption peak at 453 nm in FIG. 6 is a peak which is characteristic to such a monomer. On the contrary, in the spectrum data of the polymer B-7 which has been subjected to the fixation, the peak thereof corresponding to the large absorption peak of B-6, observed in pyridine solvent, is not large (refer to FIG. 5) but rather similar to the corresponding peak in the spectrum observed in chloroform solvent (refer to FIG. 4). This result indicates that the polymer fixed with covalent bonds of the present invention exists with remaining the polymer structure thereof even in a polar solvent. Therefore, it is now possible, according to the present invention, to provide a sample of a porphyrin array that allows evaluation of function in a polar environment.

GPC (CHCl$_3$, flow rate: 1.25 mL/h, detected 459.82 nm) 9.936 min; UV (CHCl$_3$): 731 (Abs.; 0.0163), 581 (0.0081), 500 (0.0364), 460 (0.0328), 427 (0.0368); (pyridine): 727 (0.0078), 665 (0.0066), 579 (0.0055), 492 (0.0212), 456 (0.0280), 433 (0.0272) nm; Fluorescence (EX=501 nm, CHCl$_3$): 817, 740 nm; MALDI-TOF MASS Calcd.: 1346 (monomer), 2692 (dimer), 038 (trimer), 5384 (tetramer), 6730 (pentamer); Found: 1346, 2692, 4039, 5388, 6742.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A porphyrin array exhibiting a two-photon absorption property, and being linked with an acetylenic bond(s), represented by formula (1-1) or (1-2):

(1-1)

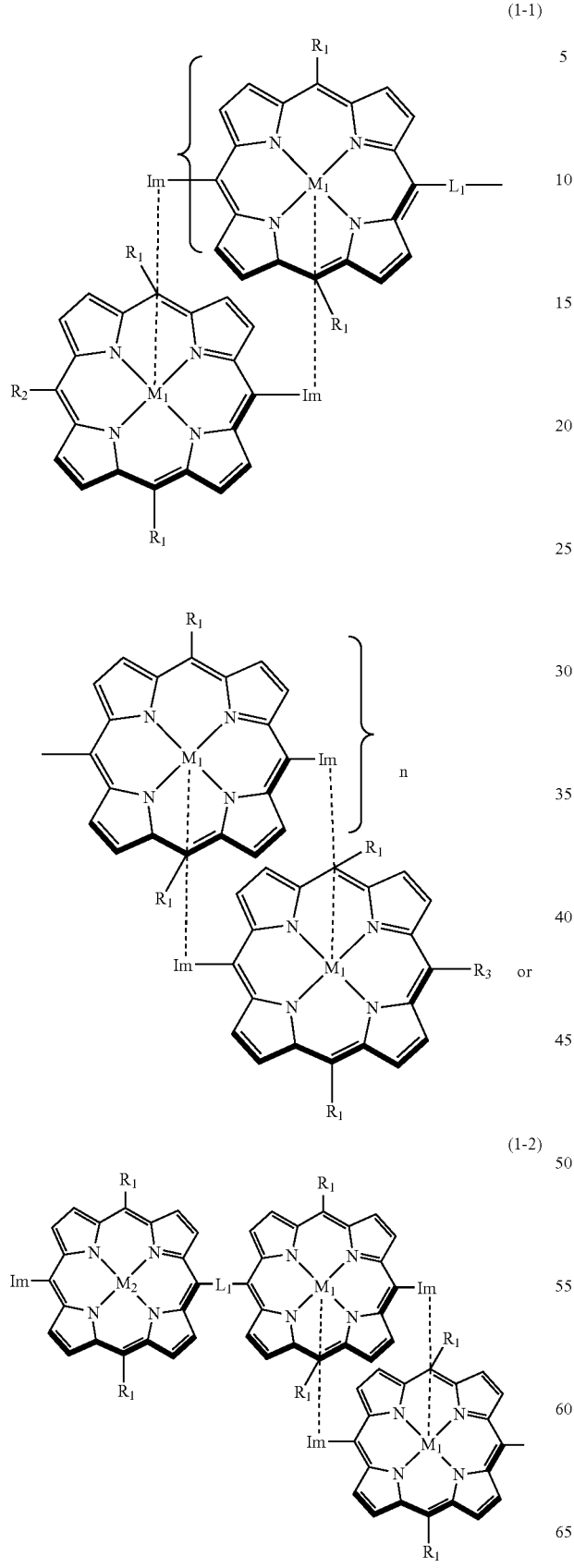

(1-2)

-continued

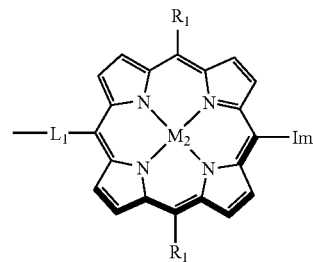

wherein

R₁ represents a substituted or unsubstituted alkyl group or substituted or unsubstituted aryl group;

M₁ represents a metal ion capable of serving as a core metal of the porphyrin ring and forming a coordinate bond with the imidazolyl group represented by Im;

M₂ represents either two protons or a metal ion incapable of forming a coordinate bond with the imidazolyl group represented by Im;

R₂ and R₃ may be the same or different, and each independently represents a group selected from the group consisting of (a) to (f):

(a) a porphyrin residue without a core metal or porphyrin complex residue having a core metal represented by M₁ or M₂, (b) a cyclic diimide residue, (c) a dialkylviologen residue, (d) a benzoquinone residue, (e) an N-methylpyrrolidine-fullerene derivative residue and (f) a ferrocene residue;

Im is an imidazolyl group represented by Im₁ or Im₂:

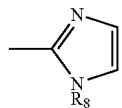   (Im₁)

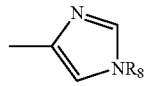   (Im₂)

wherein R₈ represents a methyl group or hydrogen atom;

L₁ represents a linking group represented by (—C≡C—)ₘ wherein m represents an integer of 1 to 3; and n represents an integer of 1 or more.

2. The porphyrin array according to claim 1, wherein the respective residues (a), (b), (c), (d), (e) and (f) are represented by:

(a)

[Structure showing two porphyrin units with M₁ and M₂ metal centers, R₁ substituents, diyne linker, and Im groups]

(b)

[Pyromellitimide/naphthalene diimide structures with R₄, R₅ substituents]

(c)

—R₆—N⁺⟨pyridyl⟩—⟨pyridyl⟩N⁺—R₇

(d)

[Benzoquinone structure]

(e)

[Fulleropyrrolidine structure with N-Me]

-continued

[Fulleropyrrolidine with p-tolyl-NH-C(O)-phenyl-N-Me substituent]

( [fullerene structure] ; fullerene (C₆₀) )

(f)

[Ferrocene structure]

wherein

R₁, M₁, M₂ and Im have the same meaning as defined in claim 1;

R₄ and R₆ each independently represent an alkylene group or arylene group; and

R₅ and R₇ each independently represent an alkyl group, alkoxyalkyl group, alkoxycarbonyl group or aryl group.

3. The porphyrin array according to claim 1, wherein M₁ is an ion of metal selected from the group consisting of zinc, iron, cobalt, ruthenium and gallium.

4. The porphyrin array according to claim 1, wherein the substituted alkyl group represented by R₁ is selected from the group consisting of an alkoxycarbonylalkyl group, alkoxyalkyl group, alkenoxyalkyl group and alkenoxycarbonylalkyl group; and the substituted aryl group represented by R₁ is selected from the group consisting of an alkylaryl group, alkoxyaryl group, alkoxycarbonylaryl group, alkenoxyaryl group and alkenoxycarbonylaryl group.

5. The porphyrin array according to claim 1, wherein the number of carbon atoms of the substituted or unsubstituted alkyl group represented by R₁ is 1 to 24; and the number of carbon atoms of the substituted or unsubstituted aryl group represented by R₁ is 6 to 24.

6. The porphyrin array according to claim 2, wherein the number of carbon atoms of the alkyl group or the alkylene group represented by R₄ to R₇ is independently selected from 1 to 20; the number of carbon atoms of the acyloxyalkyl group or the alkoxycarbonyl group represented by R₅ and R₇ is independently selected from 2 to 21; and the number of carbon atoms of the aryl group or the arylene group represented by $R_4$ to $R_7$ is independently selected from 6 to 20.

7. A method of preparing the porphyrin array represented by the formula (1-1) or (1-2) according to claim 1 comprising:

reacting, in the presence of a polar solvent, an imidazolylporphyrin metal complex represented by the following formula (2),

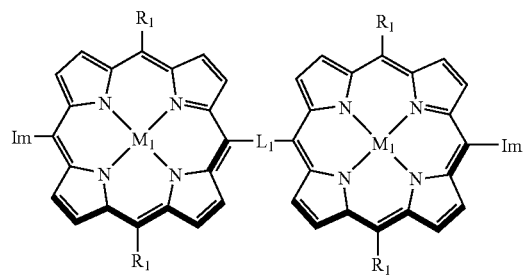

(2)

wherein $R_1$, $M_1$, $L_1$ and Im have the same meaning as defined in claim 1 with an imidazolylporphyrin metal complex represented by the following formula (3),

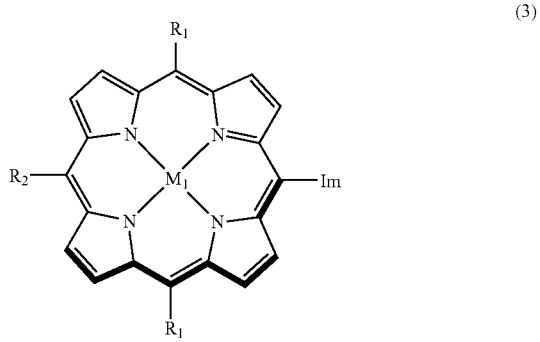

(3)

wherein $R_1$, $R_2$, $M_1$ and Im have the same meaning as defined in claim 1.

8. A porphyrin array exhibiting a two-photon absorption property, and being fixed with a covalent bond(s), represented by formula (4):

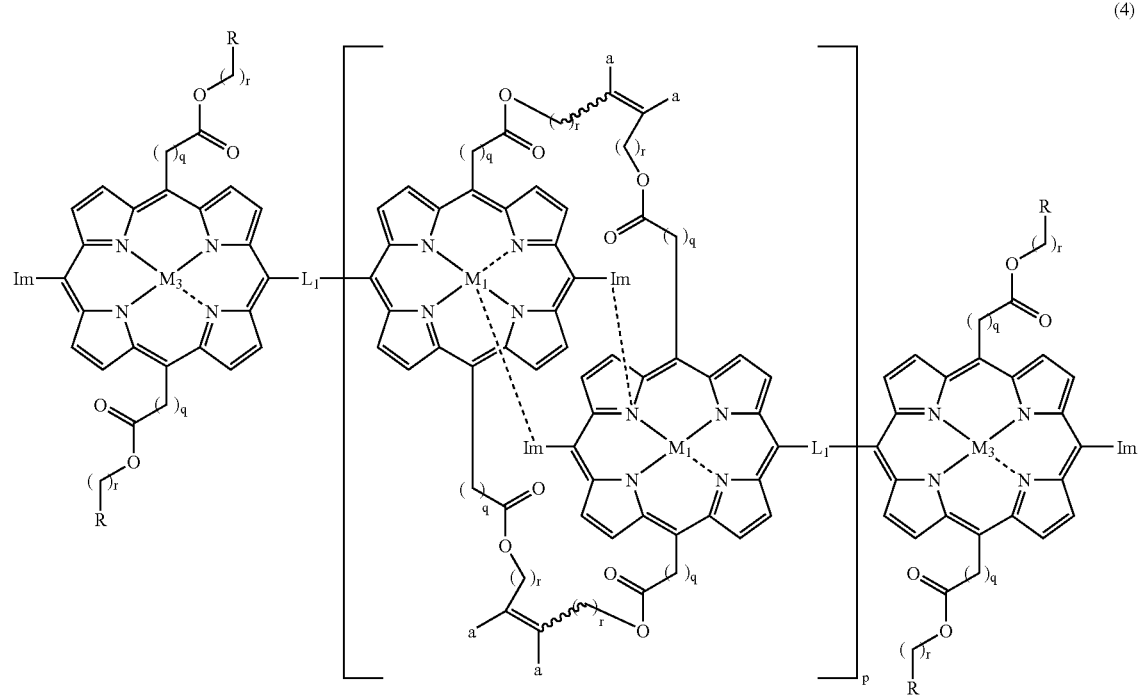

(4)

wherein R represents an alkyl group or a group as shown below:

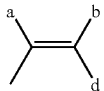

wherein a, b and c independently represent H, an alkyl group or aryl group;

$M_1$, $L_1$ and Im have the same meaning as defined in claim 1; $M_3$ represents either two protons or a metal ion selected from the group consisting of those represented by $M_1$ and $M_2$; p represents an integer of 1 or more; q represents an integer of 0 to 6; and r represents an integer of 0 to 4.

9. The porphyrin array according to claim 4, where the substituted alkyl group represented by $R_1$ is at least one selected from the group consisting of 4-methylphenyl, 4-methoxyphenyl, 4-(ethoxycarbonyl)-phenyl, 4-(2-propenoxy)-phenyl, and 4-(2-propenoxycarbonyl)-phenyl.

* * * * *